US012415981B2

(12) United States Patent
Gebhart et al.

(10) Patent No.: US 12,415,981 B2
(45) Date of Patent: *Sep. 16, 2025

(54) AUTOMATED COLLECTION OF A SPECIFIED NUMBER OF CELLS

(71) Applicants: Cell Microsystems, Inc., Research Triangle Park, NC (US); The University of North Carolina at Chapel Hill, Chapel Hill, NC (US)

(72) Inventors: Steven C. Gebhart, Durham, NC (US); Robert W. McClellan, Apex, NC (US); Nicholas C. Trotta, Durham, NC (US); Nancy L. Allbritton, Chapel Hill, NC (US); Peter Joseph Attayek, Durham, NC (US); Paul Michael Armistead, Durham, NC (US)

(73) Assignees: Cell Microsystems, Inc, Research Triangle Park, NC (US); The University of North Carolina at Chapel Hill, Chapel Hill, NC (US)

( * ) Notice: Subject to any disclaimer, the term of this patent is extended or adjusted under 35 U.S.C. 154(b) by 1021 days.

This patent is subject to a terminal disclaimer.

Patent file contains an affidavit/declaration under 37 CFR 1.130(b).

(21) Appl. No.: 16/347,104

(22) PCT Filed: Nov. 3, 2017

(86) PCT No.: PCT/US2017/059979
§ 371 (c)(1),
(2) Date: May 2, 2019

(87) PCT Pub. No.: WO2018/097950
PCT Pub. Date: May 31, 2018

(65) Prior Publication Data
US 2019/0256817 A1 Aug. 22, 2019

Related U.S. Application Data

(60) Provisional application No. 62/526,177, filed on Jun. 28, 2017, provisional application No. 62/430,094, (Continued)

(51) Int. Cl.
*C12M 1/36* (2006.01)
*C12M 1/00* (2006.01)
(Continued)

(52) U.S. Cl.
CPC .......... *C12M 41/48* (2013.01); *C12M 23/12* (2013.01); *C12M 41/36* (2013.01); *C12M 47/04* (2013.01); *C40B 30/06* (2013.01); *C40B 50/06* (2013.01); *C40B 60/14* (2013.01); *G01N 15/0612* (2013.01); *G01N 15/1433* (2024.01); *G01N 15/1434* (2013.01); *G01N 21/6408* (2013.01); *G01N 21/6428* (2013.01); *G01N 21/6452* (2013.01); *G01N 21/6458* (2013.01); *B01J 2219/00308* (2013.01); *B01J 2219/00317* (2013.01); *B01J 2219/00743* (2013.01); *C40B 60/12* (2013.01); *G01N 2015/1006* (2013.01); *G01N 2015/1447* (2013.01); *G01N 2015/1452* (2013.01); *G01N 2021/6439* (2013.01); *G01N 2201/129* (2013.01)

(58) Field of Classification Search
CPC .................................................. G01N 21/6428
See application file for complete search history.

(56) References Cited

U.S. PATENT DOCUMENTS 7,796,815 B2   9/2010   Muschler et al.
8,068,670 B2   11/2011   Muschler et al.
(Continued)

FOREIGN PATENT DOCUMENTS

CN   1556854 A   12/2004
CN   1650169 A   8/2005
(Continued)

OTHER PUBLICATIONS

Ogunniyi, Adebola O et al. "Screening individual hybridomas by microengraving to discover monoclonal antibodies." Nature protocols vol. 4,5 (2009): 767-82. doi:10.1038/nprot.2009.40 (Year: 2009).*
Wu, Xiaoqiang, et al. "Autofocus methods for automated microscopy." Biomedical Photonics and Optoelectronic Imaging. Vol. 4224. SPIE, 2000. (Year: 2000).*
Japanese Office Action (English Translation) Corresponding to Japanese Patent Application No. 2019-545711 dated Aug. 30, 2021.
Kwee et al., "Integrated Colony Imaging, Analysis, and Selection Device for Regenerative Medicine." SLAS Technology, vol. 22(2), pp. 217-223 (2017).
Mantripragada et al., "Automated in-process characterization and selection of cell-clones for quality and efficient cell manufacturing." Cytotechnology, vol. 72, pp. 615-627 (2020).
(Continued)

*Primary Examiner* — Larry D Riggs, II
*Assistant Examiner* — Kettip Kriangchaivech
(74) *Attorney, Agent, or Firm* — KDW FIRM PLLC

(57) ABSTRACT

Embodiments of the disclosed subject matter provide an automated method and system to isolate and collect cells using computerized analysis of images of cells and their surroundings obtained from a digital imaging device or system. Embodiments of the disclosed subject matter make use of a "microwell array," which can comprise a formed, elastomeric grid of indentations or "wells." Many, most, or all of the wells in a microwell array can contain a releasable, microfabricated element, which can be referred to as a "raft." Embodiments of the disclosed subject matter provide a system and method for cell collection that includes computerized identification and collection of rafts with isolated single cells or a specific group or groups of cells, eliminating the need for continuous human identification and selection.

17 Claims, 16 Drawing Sheets

Related U.S. Application Data filed on Dec. 5, 2016, provisional application No. 62/416,775, filed on Nov. 3, 2016, provisional application No. 62/416,773, filed on Nov. 3, 2016.

(51) Int. Cl.

| | | |
|---|---|---|
| C12M 1/32 | (2006.01) | |
| C12M 1/34 | (2006.01) | |
| C40B 30/06 | (2006.01) | |
| C40B 50/06 | (2006.01) | |
| C40B 60/14 | (2006.01) | |
| G01N 15/06 | (2006.01) | |
| G01N 15/1433 | (2024.01) | |
| G01N 15/1434 | (2024.01) | |
| G01N 21/64 | (2006.01) | |
| C40B 60/12 | (2006.01) | |
| G01N 15/10 | (2006.01) | |

(56) References Cited

U.S. PATENT DOCUMENTS

| | | | | |
|---|---|---|---|---|
| 9,041,791 | B2 * | 5/2015 | Zahniser | ........... H04N 5/23212 |
| 9,068,155 | B2 | 6/2015 | Allbritton et al. | |
| 10,564,172 | B2 | 2/2020 | Muschler et al. | |
| 2013/0065795 | A1 | 3/2013 | Allbritton et al. | |
| 2015/0251151 | A1 | 9/2015 | Allbritton et al. | |
| 2020/0080046 | A1 | 3/2020 | Gebhart et al. | |

FOREIGN PATENT DOCUMENTS

| | | | | |
|---|---|---|---|---|
| CN | 1745179 | A | 3/2006 | |
| CN | 101923037 | A | 12/2010 | |
| CN | 104884605 | A | 9/2015 | |
| EP | 3535441 | | 9/2019 | |
| JP | 2020-524480 | A | 8/2020 | |
| WO | WO-2011103143 | A1 * | 8/2011 | .......... B01J 19/0046 |
| WO | WO 2017/151582 | A1 | 9/2017 | |
| WO | WO 2018/017892 | A1 | 1/2018 | |

OTHER PUBLICATIONS

Gillet et al. "The Clinical Relevance of Cancer Cell Lines," Commentary, JNCI, vol. 105, Iss. 7, pp. 452-458 (2013).

Jinek et al. "A Programmable Dual-RNA-Guided DNA Endonuclease in Adaptive Bacterial Immunity," Science, vol. 337, pp. 816-821, 2012.

Kovarik et al. "Micro Total Analysis Systems for Cell Biology and Biochemical Assays," Author manuscript, pp. 1-49, 2013 [published in final edited form as: Anal. Chem. vol. 84, No. 2, pp. 516-540, 2012].

Sterneckert et al. "Investigating human disease using stem cell models," Nature Reviews Genetics, vol. 15, pp. 625-639 (2014).

Varadarajan et al. "A high-throughput single-cell analysis of human CD8+ T cell functions reveals discordance for cytokine secretion and cytolysis," The Journal of Clinical Investigation, vol. 121, No. 11, pp. 4322-4331 (2011).

Wilding et al. "Cancer Cell Lines for Drug Discovery and Development," Cancer Research, vol. 74, No. 9, pp. 2377-2384 (2014).

Altman et al., "Phenotypic Analysis of Antigen-Specific T Lymphocytes," Science, vol. 274, Iss. 5284, pp. 94-96 (1996).

Appay et al., "The assessment of antigen-specific CD8+ T cells through the combination of MHC class I tetramer and intracellular staining," J Immunol Methods, vol. 268, Iss. 1, pp. 9-19 (2002).

Attayek et al., "An array-based platform to select, release, and capture EBV-infected cells based on intercellular adhesion," Anal Chem., Author manuscript, available in PMC Jul. 2, 2018, pp. 1-19; published in final edited form as Anal Chem, 87(24), pp. 12281-12289 (2015).

Betts et al., "Sensitive and viable identification of antigen-specific CD8+ T cells by a flow cytometric assay for degranulation," J. Immunol Methods, vol. 281, Iss. 1-2, pp. 65-78 (2003).

Brent, "An Algorithm with Guaranteed Convergence for Finding a Minimum of a Function of One Variable," Algorithms for minimization without derivatives, Prentice-Hall, Englewood Cliffs, NJ, pp. 61-80 (1973).

Brochet et al., "IMGT/V-QUEST: the highly customized and integrated system for IG and TR standardized V-J and V-D-J sequence analysis," Nucleic Acids Res, vol. 36, pp. W503-W508 (2008).

Choi et al., "Development and Optimization of a Process for Automated Recovery of Single Cells Identified by Microengraving," Biotechnol Prog, vol. 26, No. 3, pp. 888-895 (2010).

Czerkinsky et al., "A Solid-Phase Enzyme-Linked Immunospot (ELISPOT) Assay for Enumeration of Specific Antibody-Secreting Cells," J Immunol Methods, vol. 65, No. 1-2, pp. 109-121 (1983).

Dees et al., "Dendritic cells can be rapidly expanded ex vivo and safely administered in patients with metastatic breast cancer," Cancer Immunol Immunother, vol. 53, pp. 777-785 (2004).

Ho et al., "In vitro methods for generating CD8+ T-cell clones for immunotherapy from the naive repertoire," J Immunol Methods, vol. 310, pp. 40-52 (2006).

Hochberg et al., "More Powerful Procedures for Multiple Significance Testing," Statistics in Medicine, vol. 9, pp. 811-818 (1990).

Linette et al., "Cardiovascular toxicity and titin cross-reactivity of affinity-enhanced T cells in myeloma and melanoma," Blood, vol. 122, No. 6, pp. 863-871 (2013).

Molldrem et al., "Targeted T-Cell Therapy for Human Leukemia: Cytotoxic T Lymphocytes Specific for a Peptide Derived From Proteinase 3 Preferentially Lyse Human Myeloid Leukemia Cells," Blood, vol. 88, No. 7, pp. 2450-2457 (1996).

Mollet et al., "Computer Simulations of the Energy Dissipation Rate in a Fluorescence-Activated Cell Sorter: Implications to Cells," Biotechnol Bioeng, vol. 100, No. 2, pp. 260-272 (2008).

Ng et al., "Masseter segmentation using an improved watershed algorithm with unsupervised classification," Comput Biol Med, vol. 38, Iss. 2, pp. 171-184 (2008).

Ogg et al., "Quantitation of HIV-1-Specific Cytotoxic T Lymphocytes and Plasma Load of Viral RNA," Science, vol. 279, Iss. 5359, pp. 2103-2106 (1998).

Otsu, "A Threshold Selection Method from Gray-Level Histograms," IEEE Transactions on Systems, Man, and Cybernetics, vol. SMC-9, No. 1, pp. 62-66 (1979).

Pala et al., "Flow cytometric measurement of intracellular cytokines," J Immunol Methods, vol. 243, Iss. 1-2, pp. 107-124 (2000).

Park et al., "A simple and fast algorithm for K-medoids clustering," Expert Systems with Applications, vol. 36, Iss. 2, pp. 3336-3341 (2009).

Riddell et al., "The use of anti-CD3 and anti-CD28 monoclonal antibodies to clone and expand human antigen-specific T cells," J Immunol Methods, vol. 128, Iss. 2, pp. 189-201 (1990).

Taswell, "Limiting Dilution Assays for the Determination of Immunocompetent Cell Frequencies. III. Validity Tests for the Single-Hit Poisson Model," J Immunol Methods, vol. 72, Iss. 1, pp. 29-40 (1984).

Wang et al., "Micromolded Arrays for Separation of Adherent Cells," Lab Chip, Author manuscript, available in PMC Nov. 7, 2011, pp. 1-16; published in final edited form as Lab Chip, vol. 10, No. 21, pp. 2917-2924 (2010).

Warren et al., "Therapy of relapsed leukemia after allogeneic hematopoietic cell transplantation with T cells specific for minor histocompatibility antigens," Blood, vol. 115, No. 19, pp. 3869-3878 (2010).

Shah et al., "Dynamics and evolution of B-catenin-dependent Wnt signaling revealed through massively parallel clonogenic screening," Integr. Biol., vol. 6, pp. 673-684 (2014).

Shah et al., "Small Sample Sorting of Primary Adherent Cells by Automated Micropallet Imaging and Release," Cytometry Part A, pp. 642-649 (2014).

Choi et al., "Development and Optimization of a Prcess for Automated Recovery of Single Cells Identified by Microengraving," Biotechnol. Prog., vol. 26, No. 3, pp. 888-896 (2010).

(56) References Cited

OTHER PUBLICATIONS

Kornyei et al., "Cell sorting in a Petri dish controlled by computer vision," Scientific Reports, vol. 3, pp. 1-10 (2013).
Extended European Search Report corresponding to European Patent Application No. 17873404.2 dated May 18, 2020.
Gracz et al., "A high throughput platform for stem cell-niche co-cultures and downstream gene expression analysis," Nature Cell Biology, vol. 17, No. 3, pp. 340-349 (2015).
Appay et al., "HIV-specific CD8+ T Cells Produce Antiviral Cytokines but Are Impaired in Cytolytic Function," J Exp Med, vol. 192, pp. 63-75 (2000).
Arber et al., "Survivin-specific T cell receptor targets tumor but not T cells," J Clin Invest, vol. 125, No. 1, pp. 157-168 (2015).
Brown et al., "Neo-antigens predicted by tumor genome meta-analysis correlate with increased patient survival," Genome Res, vol. 24, pp. 743-750 (2014).
Cameron et al., "Identification of a Titin-Derived HLA-A1-Presented Peptide as a Cross-Reactive Target for Engineered MAGE A3-Directed T Cells," Author Manuscript, pp. 1-24 [Published in final edited form in Sci Transl Med, vol. 5, No. 197ra103 (2013)].
Carpenter et al., "CellProfiler: image analysis software for identifying and quantifying cell phenotypes," Genome Biology, vol. 7, No. 10; Article R100, pp. 1-11 (2006).
Chapuis et al., "Transferred WT1-reactive CD8+ T cells can mediate antileukemic activity and persist in post-transplant patients," Author Manuscript, pp. 1-25 [Published in final edited form in Sci Transl Med, vol. 5, pp. 174ra127 (2013)].
Cong et al. "Multiplex Genome Engineering Using CRISPR/Cas Systems," Author Manuscript, pp. 1-9 [Published in final edited form in Science, vol. 339, No. 6121, pp. 819-823 (2013)].
Dong et al., "Accurate identification of single nucleotide variants in whole genome amplified single cells," Author manuscript, pp. 1-14 (2017). [Published in final edited form in: Nature Methods, vol. 14, No. 5, pp. 491-493 (2017)].
Dunbar et al., "Direct isolation, phenotyping and cloning of low-frequency antigen-specific cytotoxic T lymphocytes from peripheral blood," Curr Biol, vol. 8, pp. 413-416 (1998).
Edelstein et al., "Computer control of microscopes using µManager," Author manuscript, pp. 1-22 [Published in final edited form in Curr Protoc Mol Biol, Chapter 14, Unit14 20 (2010)].
Edelstein et al., "Advanced methods of microscope control using µManager software," Author manuscript, pp. 1-18 [Published in final edited form in J Biol Methods, vol. 1, No. 2 (2014)].
Gabrilovich et al., "Myeloid-derived-suppressor cells as regulators of the immune system," Nat Rev Immunol, vol. 9, No. 3, pp. 162-174 (2009).
Gach et al., "Isolation and manipulation of living adherent cells by micromolded magnetic rafts," Biomicrofluidics, vol. 5, pp. 032002-1-032002-12 (2011).
Gea-Banacloche et al., "Maintenance of Large Numbers of Virus-Specific CD8+ T Cells in HIV-Infected Progressors and Long-Term Nonprogressors," J Immunol, vol. 165, pp. 1082-1092 (2000).
Gracz et al., "A high throughput platform for stem cell-niche co-cultures and downstream gene expression analysis," Author manuscript, pp. 1-26 (2015). [Published in final edited form in: Nature Cell Biology, vol. 17, No. 3, pp. 340-349 (2015)].
Guillaume et al., "Fluorescence-Activated Cell Sorting and Cloning of Bona Fide CD8+ CTL with Reversible MHC-Peptide and Antibody Fab' Conjugates," J Immunol, vol. 177, pp. 3903-3912 (2006).
Hill et al., "Longitudinal Assessment of an ELISPOT Test for *Mycobacterium tuberculosis* Infection," PLoS Med, vol. 4, Iss. 6, e192, pp. 1061-1070 (2007).
Hunsucker et al., "Peptide/MHC tetramer-based sorting of CD8+ T cells to a leukemia antigen yields clonotypes drawn nonspecifically from an underlying restricted repertoire," Author manuscript, pp. 1-16, Published in final edited form in Cancer immunology research, vol. 3, No. 3, pp. 228-235 (2015).
IPRP with Written Opinion and International Search Report corresponding to International Application No. PCT/US2017/059979 dated May 7, 2019.

Kim et al., "Analysis of the Paired TCR α- and β-chains of Single Human T Cells," PloS one, vol. 7, Iss. 5, e37338, pp. 1-12 (2012).
Leong et al., "Correction of uneven illumination (vignetting) in digital microscopy images," J Clin Pathol, vol. 56, pp. 619-621 (2003).
Liadi et al., Cancer immunology research, "Individual Motile CD4+ T Cells Can Participate in Efficient Multikilling through Conjugation to Multiple Tumor Cells," vol. 3, No. 5, 473-482 (2015).
Malpica et al., "Applying Watershed Algorithms to the Segmentation of Clustered Nuclei," Cytometry, vol. 28, pp. 289-297 (1997).
Meyer, "Topographic distance and watershed lines," Signal processing, vol. 38, pp. 113-125 (1994).
Mills, "Regulatory T Cells: Friend or Foe in Immunity to Infection?" Nat Rev Immunol, vol. 4, pp. 841-855 (2004).
Molecular Devices Corporation, "Meta Imaging Series MetaMorph Basic Commands," Version 7.0.15 Product Manual [online], pp. 228, 238 (2006).
Notice of Publication corresponding to European Patent Application No. 17873404.2 dated Aug. 14, 2019.
Perna et al., "Interleukin 15 Provides Relief to CTLs from Regulatory T Cell-Mediated Inhibition: Implications for Adoptive T Cell-Based Therapies for Lymphoma," Author Manuscript, pp. 1-21, Published in final edited form in Clinical cancer research : an official journal of the American Association for Cancer Research, vol. 19, No. 1, pp. 106-117 (2013).
Rubio et al., "Ex vivo identification, isolation and analysis of tumor-cytolytic T cells," Nat Med, vol. 9, No. 11, pp. 1377-1382 (2003).
Seitz et al., "Reconstitution of paired T cell receptor α- and β-chains from microdissected single cells of human inflammatory tissues," Proc Natl Acad Sci U S A, vol. 103, No. 32, pp. 12057-12062 (2006).
Tran et al., "Immunogenicity of somatic mutations in human gastrointestinal cancers," Science, , vol. 350, Iss. 6266, pp. 1387-1390 (2015).
Varadarajan et al., "Rapid, efficient functional characterization and recovery of HIV-specific human CD8+ T cells using microengraving," Proc Natl Acad Sci U S A, vol. 109, No. 10, pp. 3885-3890 (2012).
Welch et al., "Selective single cell isolation for genomics using microraft arrays," Nucleic Acids Research, vol. 44, No. 17, pp. 8292-8301 (2016).
Wolfl et al., "Antigen-specific activation and cytokine-facilitated expansion of naive, human CD8+ T cells," Nat Protoc, , vol. 9, No. 4, pp. 950-966 (2014).
Yee et al., Journal of immunology, "Isolation of High Avidity Melanoma-Reactive CTL from Heterogeneous Populations Using Peptide-MHC Tetramers," vol. 162, No. 4, pp. 2227-2234 (1999).
Decision of Refusal corresponding to Japanese Patent Application No. 2019-545711 dated Feb. 1, 2022.
Meta Imaging Series MetaMorph Drop-in Commands, User's Guide, Molecular Devices, LLC, US, Version 4.6, pp. 1-1160 (2000).
Office Action (Restriction Requirement) corresponding to U.S. Appl. No. 16/570,673 dated Dec. 29, 2021.
Office Action corresponding to Chinese Patent Application No. 2017800817777 dated Apr. 28, 2022.
Office Action corresponding to European Patent Application No. 17873404.2-1001 dated May 18, 2022.
Office Action corresponding to U.S. Appl. No. 16/570,673 dated Aug. 16, 2022.
Chinese Office Action corresponding to Chinese Patent Application No. 2017800817777 dated Sep. 21, 2022.
Office Action corresponding to U.S. Appl. No. 16/570,673 dated Dec. 19, 2022.
Advisory Action and Interview Summary corresponding to U.S. Appl. No. 16/570,673 dated Jun. 13, 2023.
Office Action corresponding to Japanese Patent Application No. 2022-089408 dated Jun. 13, 2023.
Office Action corresponding to Chinese Application No. 201780081777.7 dated Jun. 1, 2023.

(56) References Cited

OTHER PUBLICATIONS

Office Action corresponding to Canadian Application No. 3,042,692 dated Aug. 18, 2023.

* cited by examiner

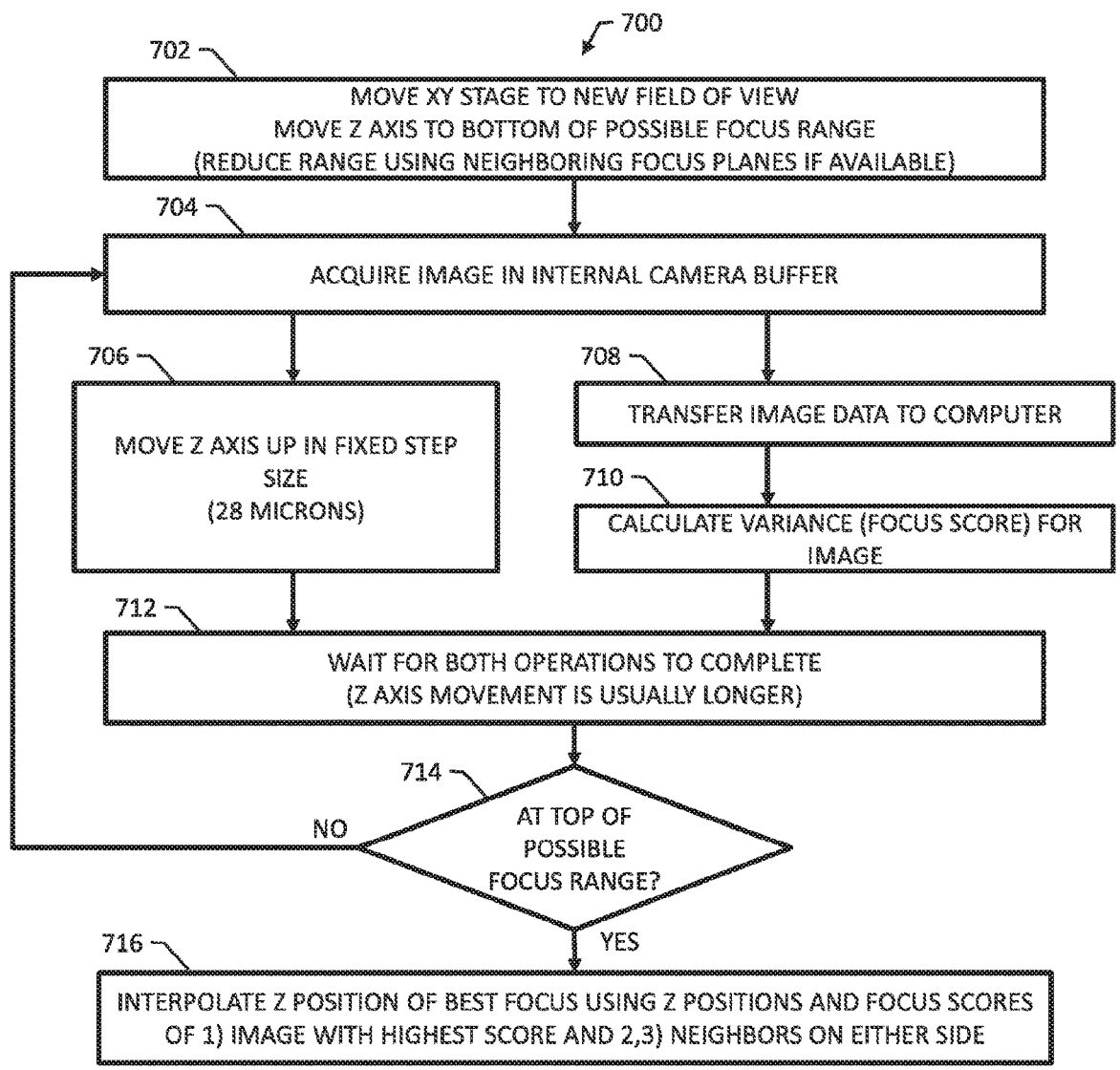
FIG. 7A
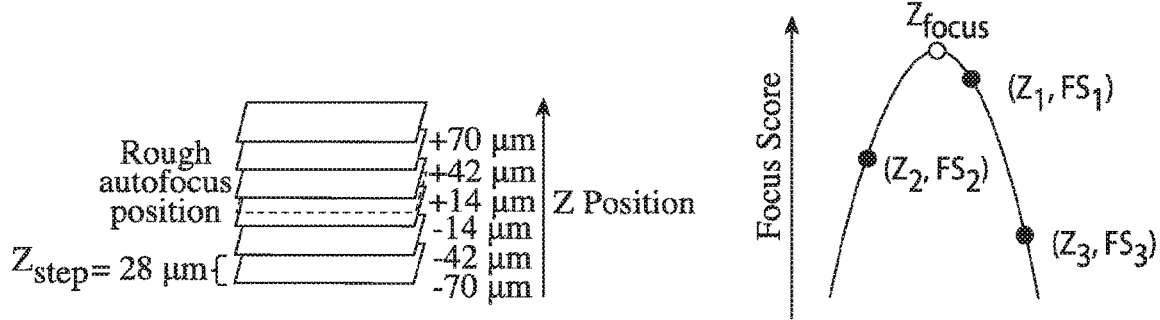
FIG. 7B
FIG. 7C

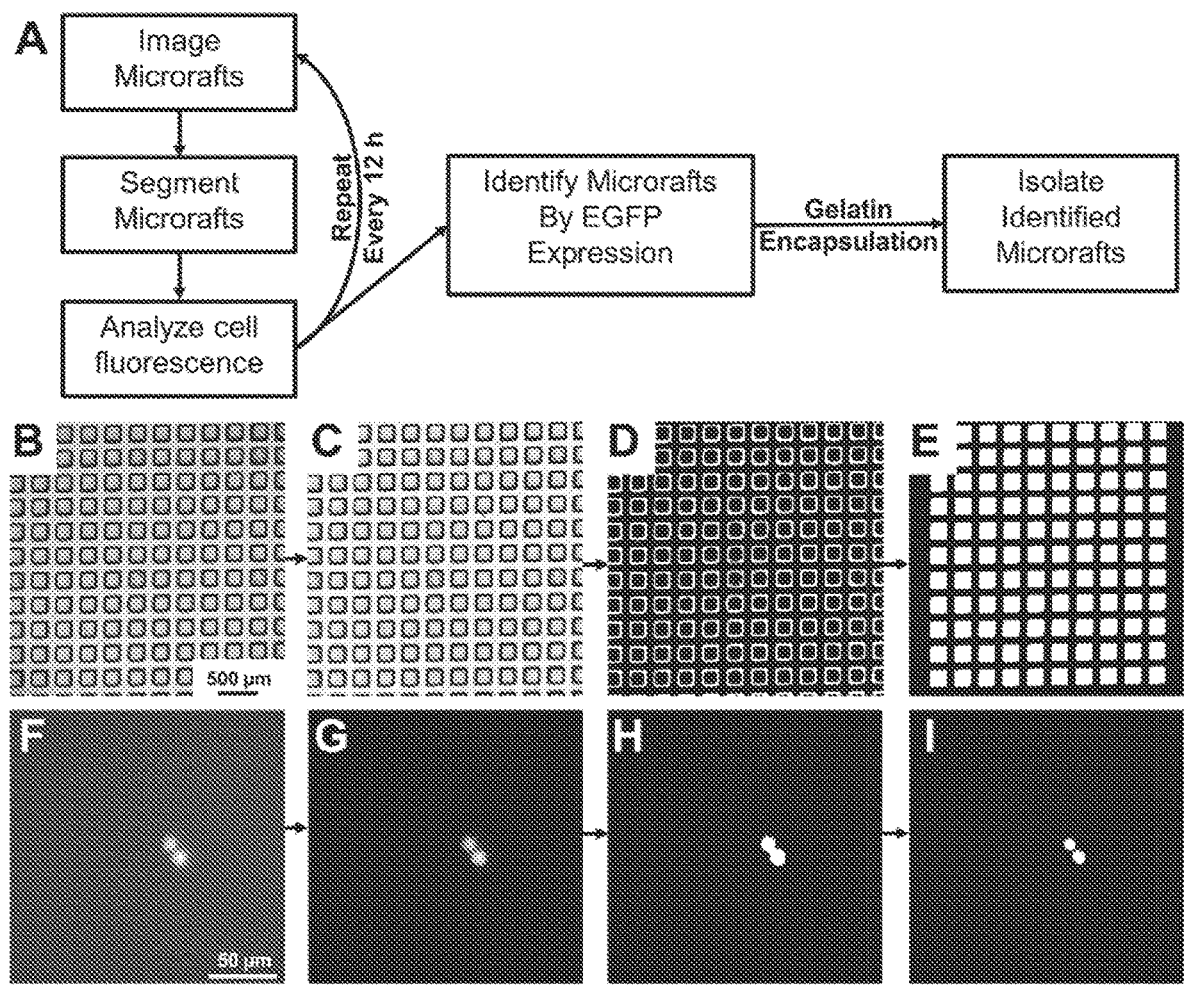
FIGS. 11A-I

AUTOMATED COLLECTION OF A SPECIFIED NUMBER OF CELLS

CROSS-REFERENCE TO RELATED APPLICATIONS

This application claims the benefit of U.S. Provisional Patent Application Ser. No. 62/416,773 filed Nov. 3, 2016, the disclosure of which is incorporated herein by reference in its entirety. This application claims the benefit of U.S. Provisional Patent Application Ser. No. 62/416,775 filed Nov. 3, 2016, the disclosure of which is incorporated herein by reference in its entirety. This application claims the benefit of U.S. Provisional Patent Application Ser. No. 62/430,094 filed Dec. 5, 2016, the disclosure of which is incorporated herein by reference in its entirety. This application claims the benefit of U.S. Provisional Patent Application Ser. No. 62/526,177 filed Jun. 28, 2017, the disclosure of which is incorporated herein by reference in its entirety.

STATEMENT REGARDING FEDERALLY SPONSORED RESEARCH

This invention was made with government support under Grant Nos. CA177993 & GM106421 awarded by the National Institutes of Health. The government has certain rights in the invention.

BACKGROUND

The selection and isolation of single cells from a mixed population is a common procedure performed throughout biomedical research. For example, during the development of cell lines that are genetically engineered, derived from stem cells, or grown from patient cell lines, single cells must be isolated and then cloned to form a homogeneous population. A variety of strategies exist to selectively identify and collect non-adherent cells from a mixed population, including fluorescence activated cell sorting (FACS), limiting dilution, panning, column chromatography and magnetic sorting; furthermore, new techniques based on microfluidics and dielectrophoresis show promise in this area. To address the need to collect pure or enriched populations of adherent cells, investigators use these procedures by disaggregating or stripping the cells from their growth surface to create cell suspensions. Unfortunately, enzymatic or mechanical release imposes significant drawbacks including loss of cell morphology, removal of cell surface markers, damage to cell membranes, alterations in cellular physiology and loss of viability.

To address this problem a cell isolation and recovery system was developed that uses polydimethylsiloxane (PDMS) microwell arrays comprising releasable, microfabricated elements, termed rafts, formed from biocompatible polystyrene or other materials. One version of such a system is called the CELLRAFT™ system. The rafts can be varied in size from tens to hundreds of microns to provide an adequate growth area for single cells or large colonies. The PDMS microwell array comprising the rafts can be visualized using, for example, an inverted microscope. Individual rafts containing the desired cells can be released from the array upon mechanical distortion of the microwell array, for example by the application of a gradual energy such as mechanical pushing or continuous vibration. In one example, individual rafts containing the desired cells can be visualized by a researcher or technician and then released from the array by mechanically pushing a probe attached to a microscope objective into the raft.

SUMMARY

Embodiments of the invention provide an automated method and system to isolate and collect cells using computerized analysis of images of cells and their surroundings obtained from a digital imaging device or system. Embodiments of the invention make use of a "microwell array," which can comprise a formed, elastomeric grid of indentations or "wells." Many, most, or all of the wells in a microwell array can contain a releasable, microfabricated element, which can be referred to as a "raft." Embodiments of the invention provide a system and method for cell collection that includes computerized identification and collection of rafts with isolated single cells or a specific group or groups of cells, eliminating the need for continuous human identification and selection.

In some examples, a system is configured for releasing cell rafts from a microwell array. The system includes an imaging device configured for obtaining images of a microwell array, an actuator configured for releasing cell rafts from the microwell array, and a computer system comprising at least one processor and memory. The computer system is programmed for: obtaining one or more images of the microwell array using the imaging device; identifying, by analyzing the one or more images of the microwell array, a selected cell raft; and controlling the actuator to release the selected cell raft from the microwell array.

The system can include one or more motors configured for moving the imaging device or the microwell array or both, and obtaining the one or more images of the microwell array can include performing an array scan by: dividing the microwell array into a plurality of fields of view such that the fields of view, collectively, include each of the cell rafts; and for each field of view, controlling the one or more motors to orient the imaging device with the field of view of the microwell array and controlling the imaging device to obtain a respective image at the field of view.

The system can include a microscope objective for the imaging system, and obtaining one or more images of the microwell array can include, for each field of view, autofocusing the microscope objective using one or more focus positions from at least one neighboring field of view. Autofocusing the microscope objective can include sampling a plurality of sample images at a plurality of sample focus positions and interpolating a current focus position from focus scores of the sample images.

Identifying the selected cell raft can include counting, for each cell raft, a number of cells depicted in a sub-image of the cell raft and identifying at least one single-cell raft bearing a single isolated cell. Counting the number of cells depicted in a sub-image comprises applying an intensity threshold to the sub-image to create a binary image, identifying unique objects in the binary image, and counting the number of identified unique objects. Identifying the single-cell raft can include determining a confidence score indicating a degree of confidence in the determination that the single-cell raft houses the single isolated cell.

Identifying the selected cell raft can include detecting, for each cell raft, a marker depicted in a sub-image of the cell raft, and gating the cell rafts based on detecting the marker. Identifying the selected cell raft can include assigning the selected cell raft to a mapped location of a collection plate. The system can include a mechanical cell raft collector, and the computer system can be configured for controlling the mechanical cell raft collector to collect the selected cell raft after release from the microwell array and for controlling the mechanical cell raft collector to deposit the selected cell raft at the mapped location of the collection plate.

In some examples, a system is configured for monitoring a cellular process. For example, the system can be configured to perform a time-course analysis of a cell or group of cells, e.g., for a drug or reagent challenge, or for changes in gene expression or cellular conditions such as cytotoxicity, cell growth, or metabolic state. The system includes an imaging device configured for obtaining images of a microwell array, the microwell array including cell rafts in microwells of the microwell array. The system includes a computer system comprising at least one processor and memory. The computer system is configured for at a first time, determining, using the imaging device, that at least one cell raft contains one or more cells undergoing a cellular process. The computer system is configured for, in response to determining that the at least one cell raft contains the one or more cells undergoing the cellular process, storing a location of the at least one cell raft on the microwell array. The computer system is configured for, at one or more times later than the first time, monitoring the cellular process by locating the at least one cell raft using the location and obtaining, using the imaging device, one or more images of the at least one cell raft.

Monitoring the cellular process can include storing the one or more images and associating each of the one or more images with a respective capture time of the image and the location of the at least one cell raft. Monitoring the cellular process can include presenting, in a graphical user interface, the one or more images and an initial image of the at least one cell raft.

Determining that the at least one cell raft contains one or more cells undergoing a cellular process can include: illuminating the at least one cell raft with light of a specified wavelength; in response to illuminating the at least one cell raft, obtaining, using the imaging device, an initial image of the at least one cell raft; and detecting a fluorescence signature of the cellular process in the initial image. Monitoring the cellular process can include presenting, in a graphical user interface, a graph of fluorescence intensity in the one or more images over time.

Determining that the at least one cell raft contains one or more cells undergoing a cellular process can include determining that the at least one cell raft is a single-cell raft containing only a single cell and quantifying a baseline fluorescence level using the initial image. Monitoring the cellular process can include determining difference in measured fluorescence between the one or more images and the initial image.

In at least some embodiments, a computer-implemented method of collecting cells includes storing information about a microwell array containing a plurality of rafts, and identifying, one or more cell rafts from among the plurality of rafts. A system like that described herein can be used to collect single-cell rafts. A single-cell raft is a raft with one isolated cell associated therewith, and often these are the cell rafts that would be selected. However, a system according to embodiments of the invention can also or instead be used to isolate rafts with some specified number of cells other than a single cell, or as another example, a raft with a single cell of one type and multiple cells of another type or a combination of specific numbers of cells of differing types. The system can then release a cell raft from the microwell array by controlling and using an actuator, and collect the cell raft using, as an example, a magnet. The system can optionally confirm a raft release prior to moving on to the next raft. Information about the microwell array can be stored in a memory device associated with or connected to a processor that executes the computer-implemented method.

In some embodiments, the storing of the information about the microwell array includes identifying and storing a size of the microwell array, identifying and storing an optimal focus position and an optimal exposure for the microwell array, and sectioning the microwell array and storing a translation required to match a set of microwells to a field of view. In some embodiments, the storing of the information about the microwell array includes calculating and storing an offset for the actuator.

In some embodiments, the identifying of the cell raft includes segmenting the plurality of rafts of the microwell array and counting the cell nuclei per raft for the plurality of rafts. In some embodiments the counting includes performing a watershed transform to define the cell nuclei relative to a fluorescence threshold. In some embodiments, the identifying of the cell rafts to be released further includes gating, or determining which of, the cell rafts are to be released by detection of a marker. As examples, a marker may include an intensity of one or more color channels (which may be indicative of fluorescence caused by a stain) and/or a size of the cell nuclei, the cell itself, or a structure other than the nucleus within the cell.

A computer system such as a workstation, personal computer, handheld computer, or embedded processing system can serve as part of the system and/or be connected to the imaging device, system and/or hardware, actuator and other equipment, and include or access non-transitory computer program code, which when executed by a processor, causes the system to execute all or a portion of the process according to example embodiments of the invention. The computer program code can be stored in a storage device.

BRIEF DESCRIPTION OF THE DRAWINGS

FIGS. 7A-7C illustrate an example method for autofocusing a microscope lens on a field of view of a microwell array.

FIGS. 11A-11I are a block diagram (FIG. 11A) and a series of images (FIGS. 11B-11I) illustrating an example experiment.

DETAILED DESCRIPTION

Figure 1A:
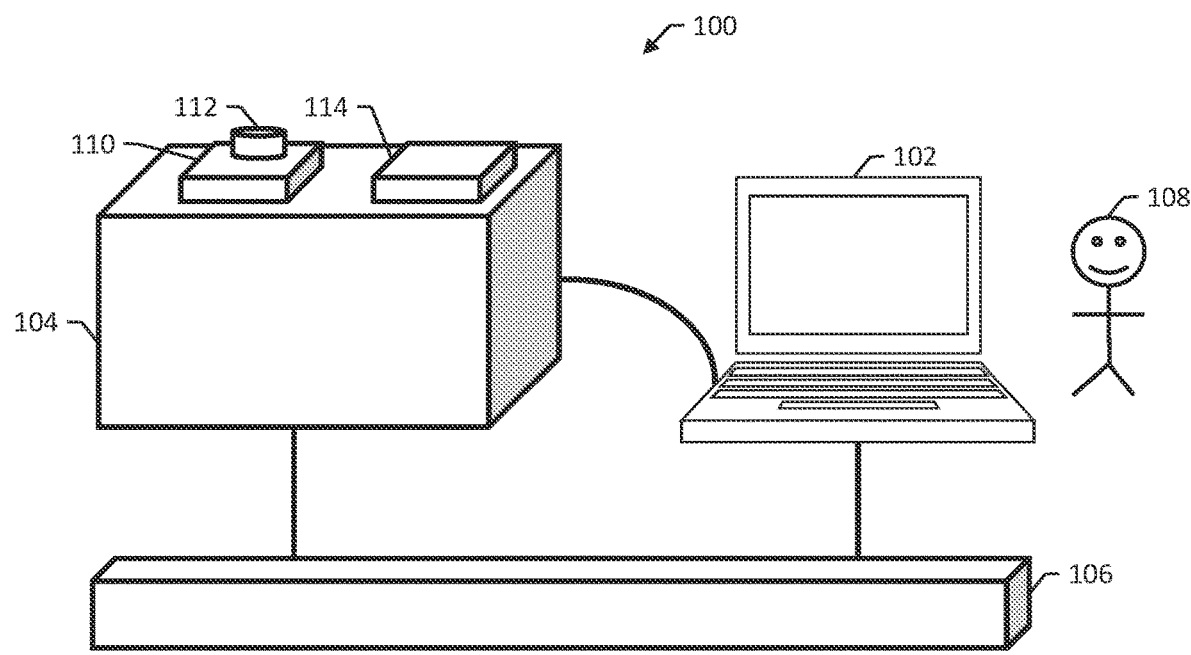
FIGS. 1A-1C are diagrams of an example system for cell collection.

Embodiments of the present invention now will be described more fully hereinafter with reference to the accompanying drawings, in which embodiments of the invention are shown. This invention may, however, be embodied in many different forms and should not be construed as limited to the embodiments set forth herein. Terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" or "comprising," when used in this specification, specify the presence of stated features, steps, operations, elements, or components, but do not preclude the presence or addition of one or more other features, steps, operations, elements, components, or groups thereof. Additionally, comparative, quantitative terms such as "above", "below", "less", "more", are intended to encompass the concept of equality, thus, "less" can mean not only "less" in the strictest mathematical sense, but also, "less than or equal to."

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein. It will also be understood that when an element is referred to as being "connected" or "coupled" to another element, it can be directly connected or coupled to the other element or intervening elements may be present.

Single cell separation can be useful for a wide variety of scientific studies including for molecular analysis of individual cells (e.g., DNA, RNA, protein) and for obtaining colonies by clonal propagation from individual cells including cells after transfection. A microwell array comprising a plurality of cell rafts in each well (a "microwell array") has been shown to be useful in single cell isolation and collection. Separating single cells by isolation and collection from microwell arrays using manual methods with a standard microscope can take a considerable amount of time when seeking to obtain a large number of single cells for analysis or propagation. Details on microwell arrays with cell rafts that can be used with a system and method of embodiments of the invention are described in U.S. Pat. No. 9,068,155, which is incorporated herein by reference. An automated system that collects cells from microwell arrays that have been seeded with cells of interest can reduce the time and labor for conducting scientific and medical studies with single cells while also including additional features such as imaging across multiple fluorescence channels.

A system for collecting cells, according to example embodiments of the invention includes an actuator, an imaging device, and a processor connected to the actuator and the imaging device, the processor being operable by use of stored executable computer program code to perform computer-implemented methods, e.g., as shown in FIGS. 3A-3B, 4A-4E, 5-6, 7A, and 8. The method and system of embodiments of the invention is presented in the figures by way of example as identifying single, isolated cells present on individual cell rafts in the microwell array, and collecting those cells by way of collecting single-cell rafts.

Figure 1B:
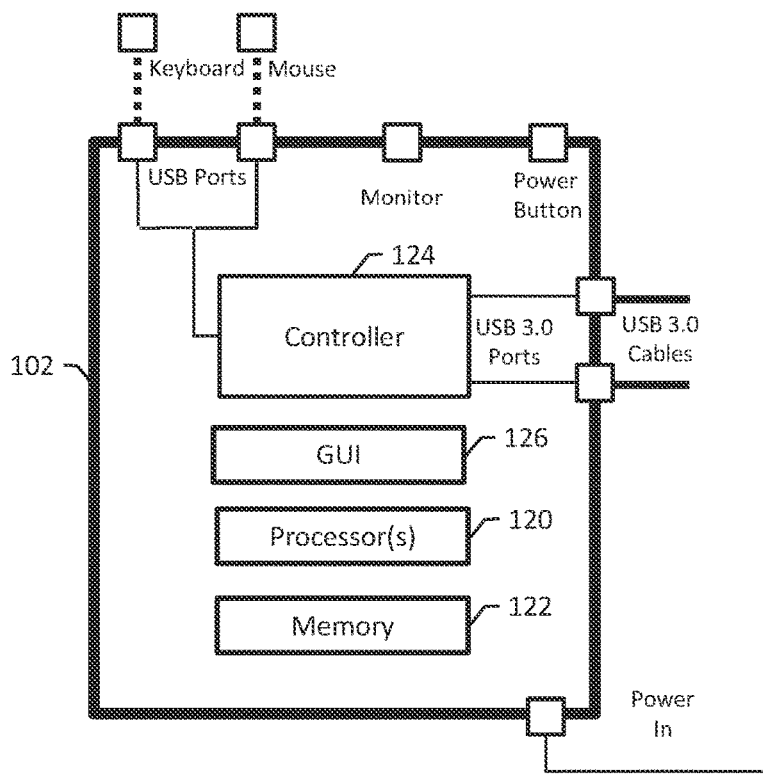
Figure 1C:
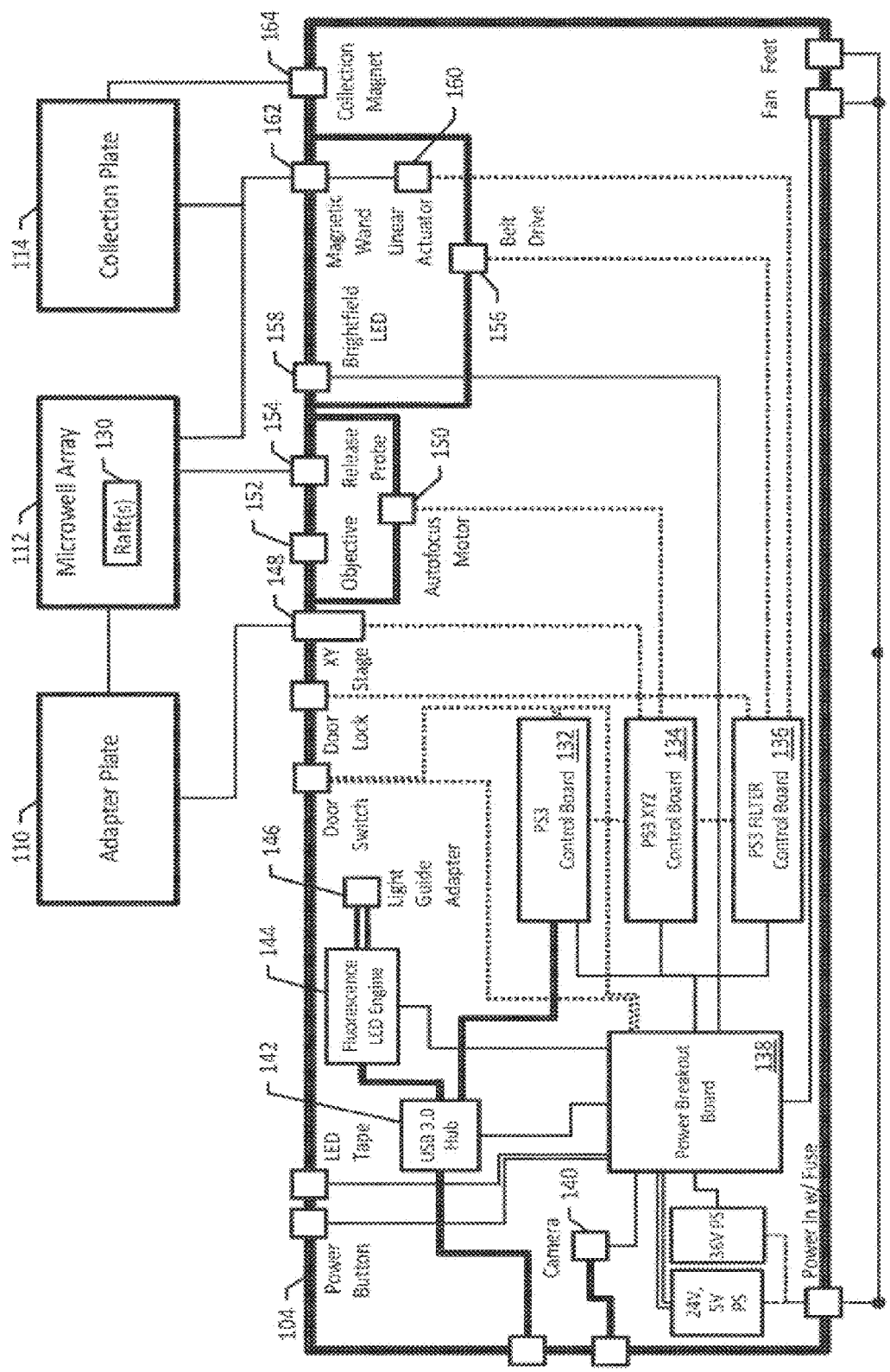

FIGS. 1A-1C are diagrams of an example system 100 for cell collection. The system 100 can be used to identify and collect multiple cells, cell colonies and rafts with various numbers of cells of different types. FIG. 1A is an overview diagram of the system 100. The system 100 includes a computer system 102, an instrument assembly 104, an experimental environment 106 (e.g., one or more pieces of laboratory equipment such as power supplies and environmental control systems), and a user 108. The instrument assembly 104 includes an optional adapter plate for receiving a microwell array 112 and a collection plate 114 for receiving cell rafts that have been selected and released from the microwell array 112. The collection plate 114 can be organized into a standardized format, e.g., as an SBS collection plate. Although a collection plate 114 is shown, the system 100 can alternatively use any appropriate collection structure, such as PCR strip tubes.

Typically, the user 108 would load or seed cells in media on the microwell array 112 and allow the cells to settle into individual cell rafts. The microwell array 112 is then placed into the adapter plate 110 of the system 100 for scanning and image analysis. The system 100 can then release a cell raft from the microwell array 112 by controlling and using an actuator, and collect the cell raft with the isolated cell using, as an example, a magnet. For example, the actuator can be one or more motors configured to move a needle or similar device to release rafts. In some examples, the system 100 includes multiple actuators, including, possibly another actuator to move a magnetic wand, and possibly actuators to move a stage, imaging optics, and other mechanical parts of the system.

FIG. 1B is a block diagram of the computer system 102. The computer system 102 includes at least one processor 120, memory 122, a controller 124 implemented as a computer program using the processor 120 and memory 122, and a graphical user interface (GUI) 126. For example, the computer system 102 can be a desktop computer with a monitor and keyboard and mouse, or the computer system 102 can be a laptop or tablet computer or any other appropriate device. The computer system 102 is operatively coupled to the instrument assembly 104, e.g., by universal serial bus (USB) cables.

The controller 124 is programmed for obtaining one or more images of the microwell array 112; identifying, by analyzing the images, a selected cell raft of the microwell array 112; and controlling the instrument assembly 104 to release the selected cell raft. The controller 124 can perform the example methods described further with references to FIGS. 3A-3B, 4A-4E, 5-6, 7A, and 8. The GUI 126 is configured to present various control and results screens to the user 108 and to receive input from the user 108.

FIG. 1C is a block diagram of the instrument assembly 104. The instrument assembly 104 can include various components for imaging individual cell rafts 130 on the microwell array 130 and selectively releasing cell rafts 130 from the microwell array for placement into the collection plate 114. For example, the instrument assembly 104 can include a power breakout board 138 and various control boards for controlling motors and actuators (e.g., PS3 control board 132, PS3 XYZ control board 134, and PS3 FILTER control board 136). The motor control boards can contain TTL and shutter functions that allow the controller 124 to control or address various components of the instrument assembly 104.

The instrument assembly 104 can include a digital camera 140 or other appropriate imaging device, a communications hub (e.g., USB Hub 142), a fluorescence light emitting diode (LED) engine 144, and a light guide adapter 146. The fluorescence LED engine 144 can include multiple narrow-band LEDs configured to illuminate the microwell array 112 by way of the light guide adapter 146.

The instrument assembly 104 includes a microscope system (e.g., an internal inverted digital microscope) including a motorized XY stage 148 and an autofocus motor 150 configured for translating a microscope objective 152. Typically, the camera 140 and the fluorescence LED engine 144 and microscope system are arranged in an epi-fluorescence configuration. In some examples, the microscope system includes a release probe 154 configured for individually releasing cell rafts 130 from the microwell array 112. The release probe 154 can be actuated by the autofocus motor 150.

In some examples, the microscope system supports imaging of a region at least about 4×4 array features on a microwell array having rafts of 200 micron×200 micron in dimension and approximately 8×8 array features if the rafts have a 100 micron×100 micron array in a given field of view at a resolution of less than 2 microns per pixel. The microscope system may also support the capture of images using brightfield imaging (i.e. white light illumination and white light emission) and the capture of images in one or more fluorescent emission channels. In some examples, the instrument assembly 104 is capable of scanning an entire microwell array in under 20 minutes for all three fluorescent channels and brightfield assuming an exposure time 750 ms across all channels.

The release probe 154 typically comprises materials resistant to oxidation when exposed to saline or cell culture media. In some examples, the release probe 154 is a stainless steel 100 micron needle. The release probe 154 can have a possible travel distance of, e.g., at least 15 mm in the X and Y directions with respect to the center of the microwell array 112.

The instrument assembly 104 includes a gantry assembly including a belt drive 156 for moving the gantry assembly, a brightfield LED 158 for illuminating the microwell array 112 during imaging, and a linear actuator 160 configured for moving a magnetic wand 162 to collect cell rafts after release. The gantry assembly can alternatively use a lead screw instead of a belt drive, or any other appropriate motor. The linear actuator 160 can be, e.g., a stepper motor configured to raise and lower the magnetic wand 162 into and out of the microwell array 112 and the collection plate 104.

The instrument assembly 104 includes a collection magnet 164 positioned underneath the collection plate 114 to collect cell rafts into the collection plate 114 from the magnetic wand 162. The collection magnet 164 can have a polarization opposite that of the magnetic wand 162 to repel the magnets within the magnetic wand 162 and pull the cell raft to the bottom of the collection plate 104. The magnetic wand 162 typically comprises a material that is capable of being rendered sterile (e.g., rinsed with ethanol or isopropanol while removed from the instrument) so as not to contaminate the released cell raft or the media used in the collection plate 104. The material for the magnetic wand 162 is also generally selected such that contact with the culture media does not cause any detectable decrement in cell viability or proliferation, or in the performance of molecular biology reagents, such as Taq polymerase, or reverse transcriptase.

Figure 2A:
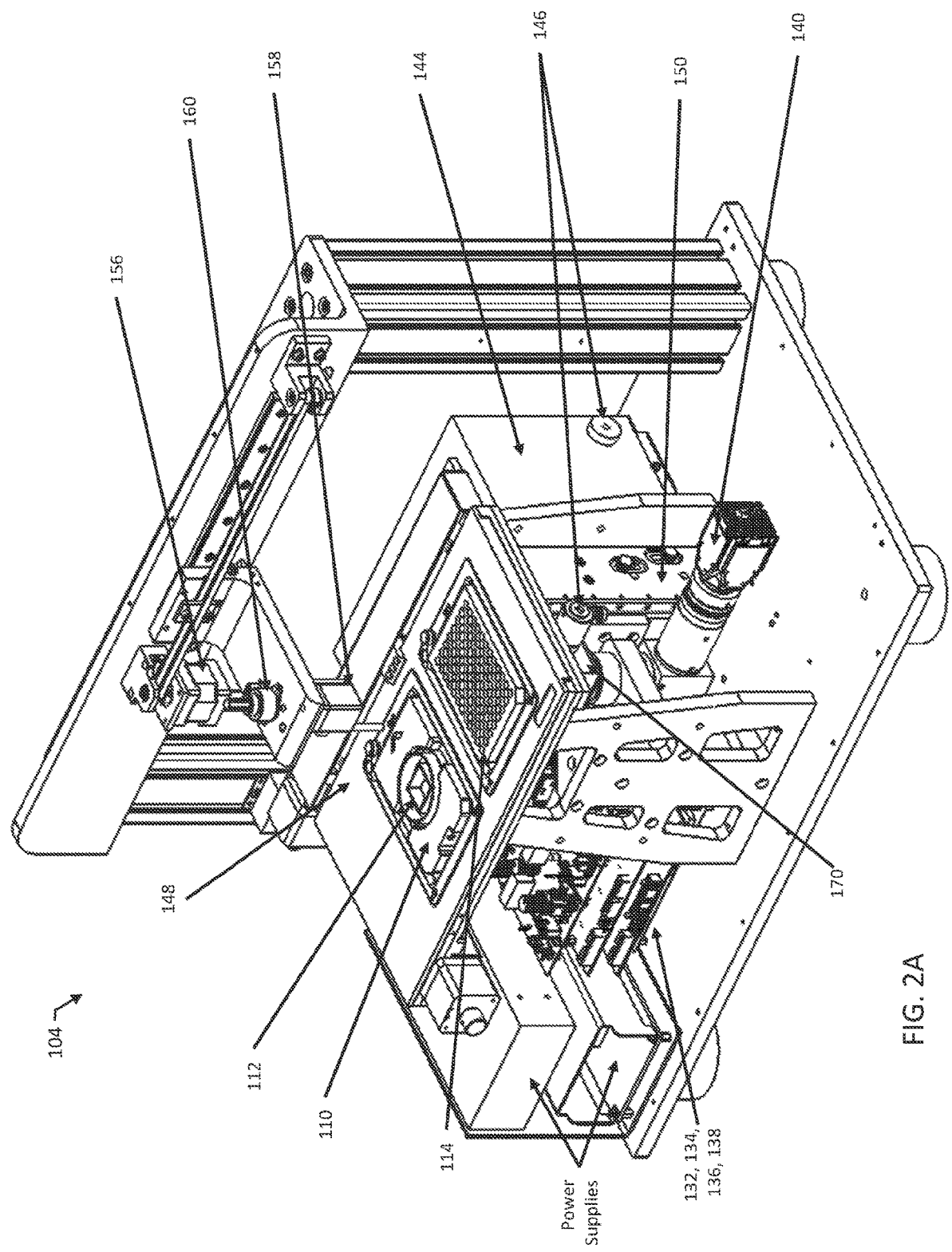
FIGS. 2A-2B are isometric views of an example apparatus for cell collection.
Figure 2B:
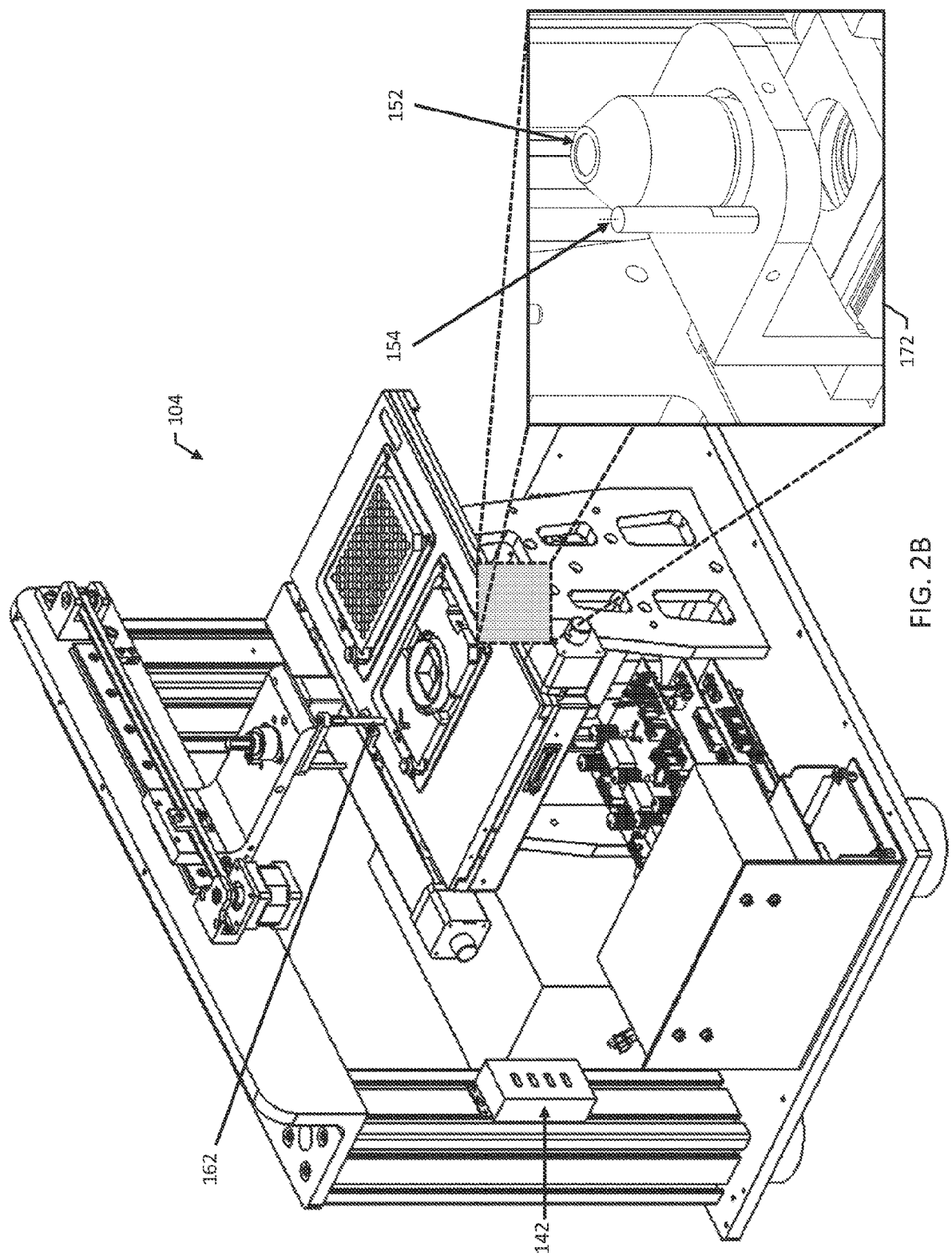

FIGS. 2A-2B are isometric views of an example apparatus for cell collection. The apparatus is an example implementation of the instrument assembly 104 depicted in FIG. 1C. As shown in FIG. 2A, the adapter plate 110 and the collection plate 114 are positioned on top of the horizontal XY stage 148. Some components, such as the electronic control boards 132, 134, and 136 are located below the XY stage 148. The XY stage 148 is configured to move the microwell array 112 and the collection plate 104. The XY stage 148 is electronically controllable for positioning cell rafts for imaging (aligning cell rafts with the microscope objective 152), releasing cell rafts (aligning cell rafts with the release probe 154), and depositing cell rafts (aligning the magnetic wand 162 and selected locations of the collection plate 104 over the collection magnet 164).

The gantry assembly, including the belt drive 156, is positioned vertically over the XY stage 148. The gantry assembly is configured to move laterally to position the brightfield LED 158 for imaging and also to position the magnetic wand 162. The gantry assembly positions the magnetic wand 162 over the microwell array 112 to collect rafts during release, and then the gantry assembly positions the magnetic wand 162 over the collection plate 114 to deposit cell rafts into selected locations of the collection plate 114.

The camera 140 and the autofocus motor 150 are located beneath the XY stage 148, e.g., so that the autofocus motor 150 can move vertically with respect to the XY stage 148. The fluorescence LED engine 144 and liquid light guide ports 146 are located below the XY stage 148 and coupled to a fluorescence filter cube 170. The fluorescence filter cube 170 is configured for fluorescence imaging, e.g., to allow light from the fluorescence LED engine 144 to reach the microwell array 112 and to block that light from reaching the camera 140.

FIG. 2B shows a cut-away view 172 of the microscope objective 152 and the release needle 154. As shown, the release probe 154 is offset from the optical axis of the microscope objective 152, such that the release probe 154 does not intersect the field of view of the microscope objective 152. With the release probe 154 not intersecting the field of view, a user may not be able to visualize release of a cell raft in real time, such that the system may have to move the microwell array 112 after release to confirm release by imaging. Nonetheless, it can be useful to position the release probe 154 outside the field of view of the microscope objective 152 to improve imaging speed.

In some other examples, the release probe 154 is located within the field of view of the microscope objective 152. Locating the release probe 154 in the field of view of the microscope objective 152 allows a user to visualize the release of a cell raft in real time; however, such a location can require imaging through the acrylic window, which can reduce the transmission of the excitation and emission light and require longer integration times during scanning.

In either case, it can be useful to calibrate the offset between the center of the field of view of the microscope objective 152 and the puncture location of the release probe 154 on the microwell array 112. Calibration can be performed, e.g., after every needle replacement, or at the start of every experiment, or one time during manufacturing. In some examples, the controller 124 of FIG. 1B is programmed to perform automated calibration.

For example, the controller 124 can move the microwell array 112 to position the field of view of the microscope objective 152 with an array border, autofocus the microscope objective, and then puncture the array border with the release probe 154. Then, the controller 124 moves the microwell array 112 to position the puncture location within the field of view of the microscope objective 152, acquires an image (e.g., using the brightfield LED 158), and analyzes the image to locate the puncture position, e.g., by segmenting the image. The controller 124 can then calculate an offset. In some examples, the controller 124 repeats the process a specified number of times by moving to different locations and determines a calibration distance based on the offset positions, e.g., by averaging the offset positions.

Figure 3A:
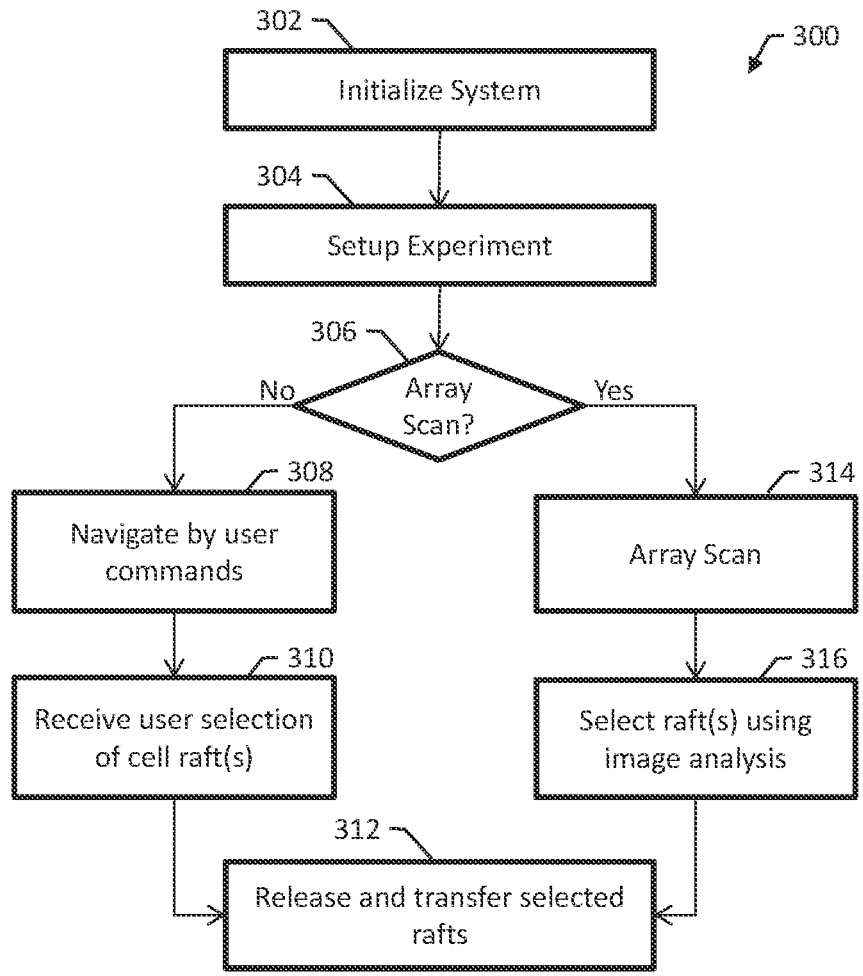
FIGS. 3A-3B illustrate an example method for cell collection.
Figure 3B:
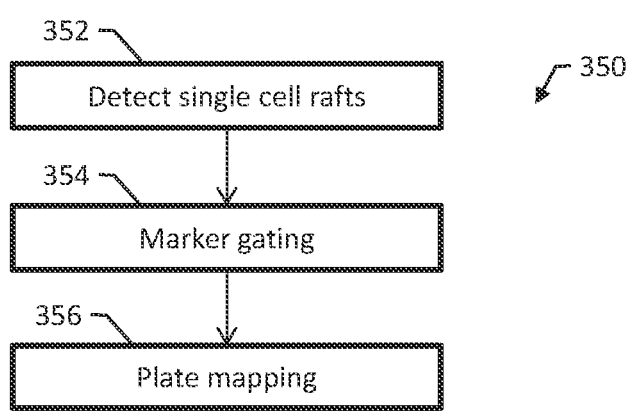

FIGS. 3A-3B illustrate an example method for cell collection. FIG. 3A is a flow diagram of the example method 300 for cell collection from a microwell array. The method 300 can be performed by the controller 124 of FIG. 1, and the method 300 will be described with respect to the system 100 of FIG. 1.

The method 300 includes initializing the system (302) and setting up an experiment (304), which are described further below with reference to FIGS. 4A-4B.

The method 300 includes determining whether to perform an array scan (306), e.g., by prompting the user 108 using the GUI 126. If not performing an array scan, the method 300 includes navigating the microwell array 112 by user commands (308), e.g., received using the GUI 126. Navigating by user commands can include presenting images of the microwell 122 array in real-time as the user navigates the microwell array 112. The method 300 then includes receiving a user selection of one or more cell rafts for cell collection (310), e.g., selected using the GUI 126.

If performing the array scan, the method 300 includes performing the array scan by navigating the microwell array 112 without user input (314). The method 300 then includes selecting one or more cell rafts for cell collection using image analysis (316). FIG. 3B is a flow chart of an example method 350 for selecting cell rafts using image analysis. The method 350 includes detecting single cell rafts (352), gating the single cell rafts based on marker detection (354), and mapping the gated single cell rafts to locations on a collection plate (356). Gating the single cell rafts generally includes selecting a subset of detected single cell rafts based on detection of fluorescence markers.

Array scanning, single-cell detection, and automated or semi-automated cell raft selection are described further below with reference to FIGS. 4C-4D. In some examples, the array scan and identifying the cell rafts are performed in parallel. For example, the controller 124 can execute multiple threads in parallel, or use any appropriate parallel processing technique.

The method 300 includes releasing and transferring the selected cell rafts (312). Release and transfer are described further below with reference to FIG. 4E. The method 300 can optionally include exporting data describing an experiment, e.g., user input received, images captured, locations of detected single-cell rafts, records of released cell rafts, and any other appropriate data. Exporting data can include storing the data in a file on a local filesystem or transmitting the data to a remote system for storage.

As can be seen in FIGS. 3A-3B, a system according to example embodiments can be used in a manual selection mode where the user identifies single cell rafts during real-time imaging ("real time imaging mode") which may include storing such images in a memory device, but can also be used for a computer-implemented method of collecting cells, referred to as a "cytometric image analysis" mode. In accordance with some embodiments, the user 108 selects through the GUI 126 to operate the system 100 in cytometric image analysis mode or real-time imaging mode. In real-time imaging mode, the user 108 is able to selectively navigate the imaging field of view within the microwell array 112 and select rafts for isolation based on visual inspection of real-time images. In cytometric image analysis mode, a full scan of the microwell array is performed, and then quantitative image processing (e.g., of the fluorescence images) facilitates user selection of cells for isolation or automated selection of cells for collection.

In the cytometric image analysis mode, the system scans a microwell array and stores, in a memory device, information about a microwell array containing a plurality of rafts, identifies, using a processor to perform image analysis and using the information, a cell raft having one or more cells from among the plurality of rafts, and releases, using the processor and an actuator, the cell raft from the microwell array. In some embodiments, the storing of the information about the microwell array includes calculating and storing an offset for the actuator. In some embodiments, the system determines an address for each of a plurality of the microwells in the microwell array in order to expedite future operations by relying on known positions of specific rafts. The system can perform gating of the cell rafts to be released by the actuator based on detection of a marker, for example, based on intensity of a fluorescent color or brightfield channel as determined from the imaging device, a size of a cell nucleus or other structure, or a combination of these markers. In some embodiments, the system collects cell rafts containing magnetic nanoparticles using a magnet and can optionally confirm that the cell raft has in fact been released.

FIGS. 4A-4E are workflow diagrams showing interactions between user inputs, graphical user interface functions, hardware, and software for a system according to example embodiments of the invention. The workflow diagrams will be described with reference to the example system 100 of FIG. 1. Each workflow diagram is horizontally divided into four regions. The top-most region shows actions performed by the user 108. The region below the top-most region shows actions carried out using the GUI 126. The next region shows actions carried out using hardware (e.g., the instrument assembly 104). The bottom-most region shows actions performed by the controller 124.

Figure 4A:
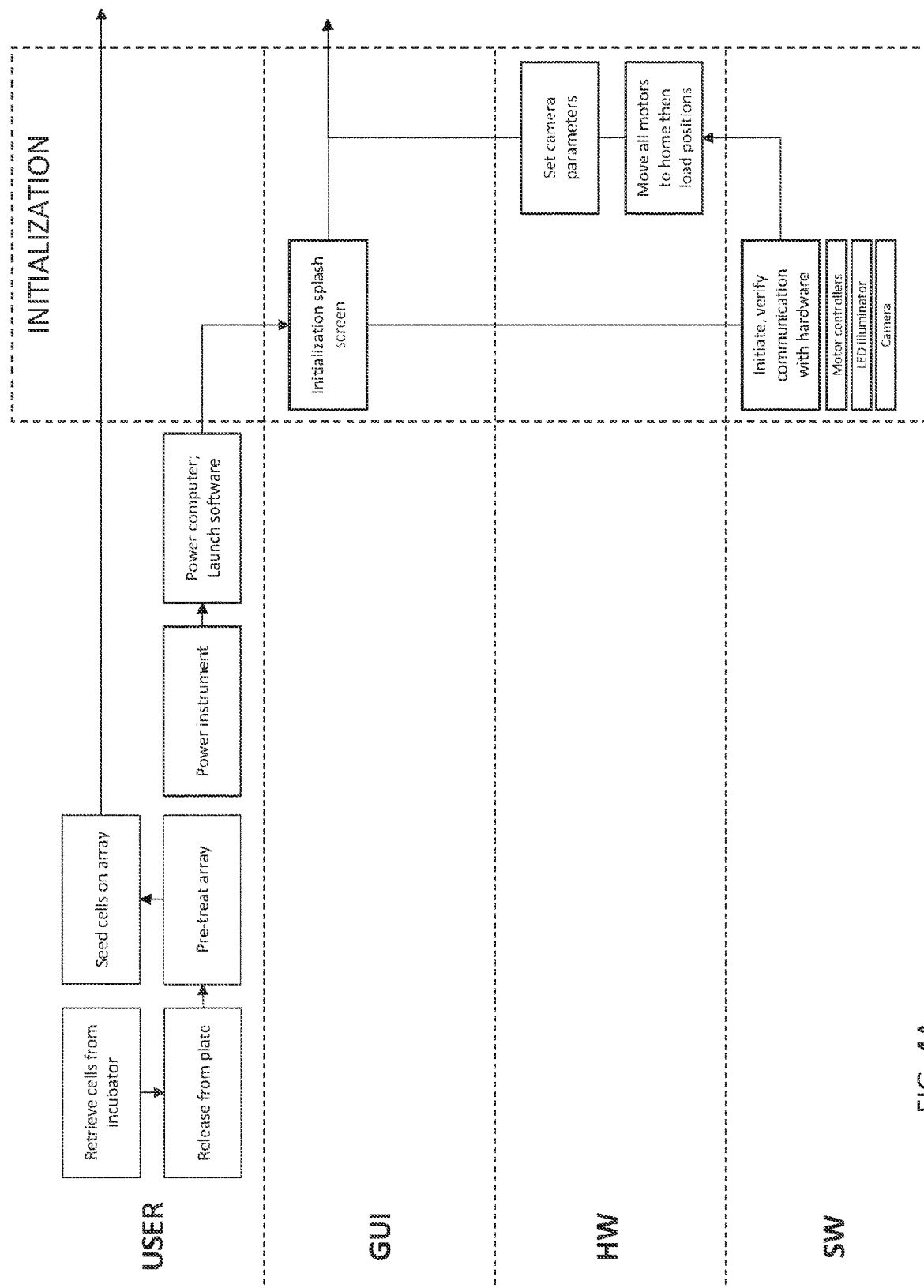
FIGS. 4A-4E are workflow diagrams showing interactions between user inputs, graphical user interface functions, hardware, and software for a system according to example embodiments of the invention.

FIG. 4A illustrates the beginning of an example experiment. The user 108 retrieves cells, e.g., from an incubator and releases the cells from a plate. The user 108 pre-treats a microwell array 112 and seeds cells on the microwell array 112. The user 108 powers the instrument assembly 104 and the computer system 102 and launches the controller 124 and the GUI 126. During initialization, the GUI 126 can display an initialization splash screen, while the instrument assembly 104 sets camera parameters and moves motors to home and then load positions. The controller 124 initiates and verifies communication with the instrument assembly 104, including the motor controllers, LED illuminator, and camera.

Figure 4B:
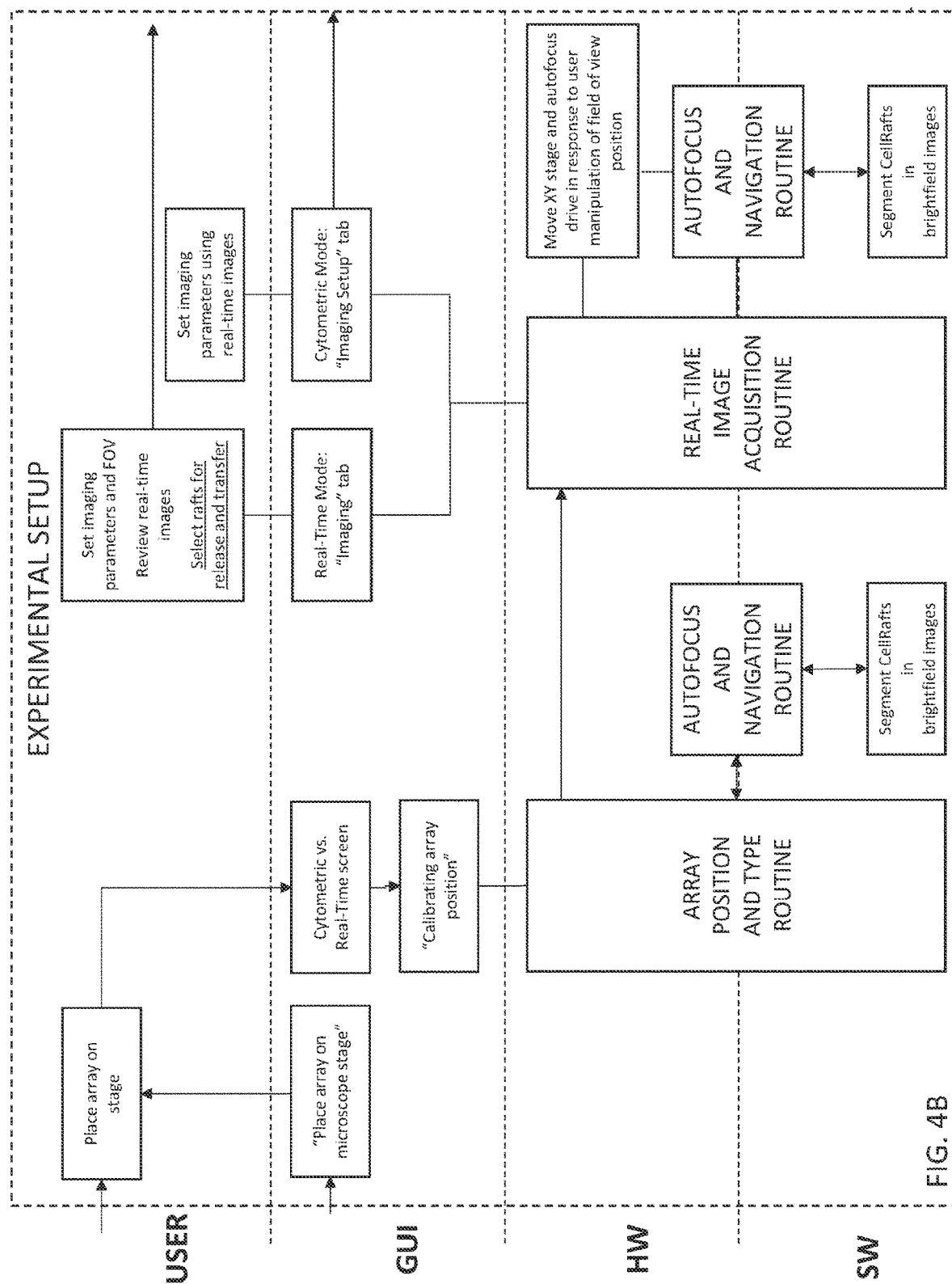

FIG. 4B illustrates the next stage of the example experiment, experimental setup. The GUI 126 prompts the user 108 to place the microwell array 112 on the microscope stage. The user 108 places the microwell array 112 on the XY stage 148 (e.g., onto the adapter plate 110). The GUI 126 prompts the user 108 to select either a cytometric mode or a real-time analysis mode, receives a selection from the user 108, and then displays a screen indicating the system is calibrating an array position for the microwell array 112.

The controller 124 executes an array position and type routine, which includes controlling the instrument assembly 104 to obtain images of the microwell array 112 and identifying the orientation of the microwell array 112 and the type of microwell array 112. The type of the microwell array 112 can characterize, e.g., the number and size of cell rafts on the microwell array 112. The array position and type routine can include performing an autofocus and navigation routine and identifying cell rafts, e.g., by performing image segmentation on brightfield images. An example array position and type routine is described further below with reference to FIG. 5. In some examples, the system 100 provides the user 108 with user interface controls to control stage motors and visual feedback of brightfield images to position the corner of the microwell array 112 within the field of view and click on it to identify the array position and type.

If the user 108 selected the real-time imaging mode, then the controller 124 executes a real-time image acquisition routine. The user 108 sets imaging parameters and the field of view and reviews images in real-time, i.e., images as the instrument assembly 104 navigates the microwell array 112. The controller 124 controls the XY stage 148 and autofocus motor 150 in response to user input from the GUI 126 manipulating the field of view position. The controller 124 executes the autofocus and navigation routine to navigate the microwell array 112, and at new fields of view, identifies cell rafts. The user 108, after reviewing the images, selects one or more cell rafts for release and transfer. If the user 108 selected the cytometric imaging mode, the GUI 126 optionally presents a screen for the user 108 to set imaging parameters for the array scan. The imaging parameters can alternatively be read from a file or receiving over a network connection.

Figure 4C:
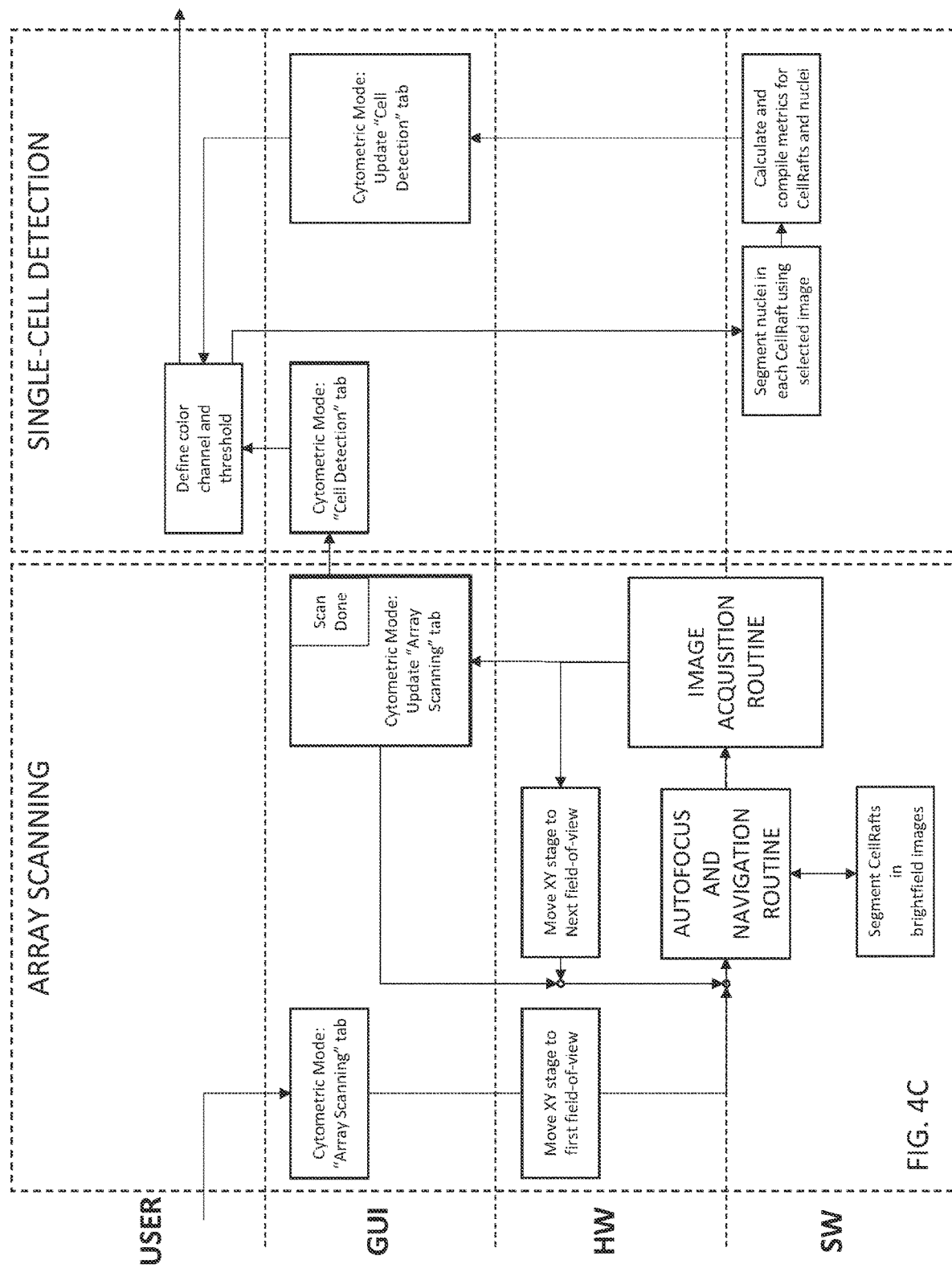

FIG. 4C illustrates the next stage of the example experiment if the user 108 selected the cytometric mode, array scanning and single-cell detection. The GUI 126 optionally presents a status screen during the array scan. The controller 124 divides the array extent into discrete fields of view, e.g., by maximizing the number of cell rafts within each field of view (i.e., minimizing the number of fields of view) while ensuring that no cell rafts are missed.

In general, the controller 124 uses an iterative state positioning and raft segmentation process to optimize the position of rafts within each field of view to maximize the number of cell rafts in each field of view and to calculate the translation required to image next set of cell rafts. The controller 124 can perform the iterative stage positioning and raft segmentation based on, e.g., the consistency of cell raft dimensions and spacing in arrays; a nominal margin between full cell rafts within a field of view and edges of the field of view; precision of state motor movements; and computational time to detect cell rafts within images. Alternatively, the controller 124 can translate a given distance between fields of view that ensures that at least one cell raft width of overlap and resolve duplicate cell raft images during processing.

The instrument assembly 104 moves the XY stage 148 to a first field of view. The controller 124 executes the autofocus and navigation routine, which can include identifying the cell rafts in the field of view, and then the controller 124 executes the image acquisition routine. The image acquisition routine can include lighting one or more specific light sources depending on the imaging parameters, e.g., whether a particular fluorescence channel is specified, and then controlling the camera 140 as specified, e.g., for a particular exposure time.

The controller 124 then controls the XY stage 148 to move to a next field of view and repeats the autofocus and navigation routine and image acquisition routine. The array scan continues until an end condition is reached, e.g., the entire microwell array 112 or a specified portion of the microwell array 112 has been imaged or a time limit is reached. The array scan can proceed in any appropriate directional manner, e.g., processing a row in one direction and then processing the next row in an opposite direction.

During the array scan, the controller 124 assigns each detected cell raft an address. The addresses are useful, e.g., so that images of the cell raft and other data can be associated with the cell raft, and so that cell rafts can be located for release and transfer.

When the scan is complete, the GUI 126 presents an optional screen for receiving single-cell detection parameters from the user 108. The user 108 can input, e.g., the color channel and a threshold for the color channel. The controller 124 performs an image analysis of the images obtained during the scan to identify single-cell rafts. For example, the controller 124 can segment cell nuclei in each cell raft using extracted sub-images of selected images. Typically, an image of a field of view of the microwell array 112 will include multiple cell rafts. Extracting a sub-image of a particular cell raft can include segmenting the image to identify locations of the cell rafts and then isolating the portion of the image depicting the particular cell raft. Identifying single-cell rafts is discussed further below with reference to FIG. 8. The controller 124 can then calculate and compile metrics for cell rafts and cell nuclei segmented in the selected images.

Figure 4D:
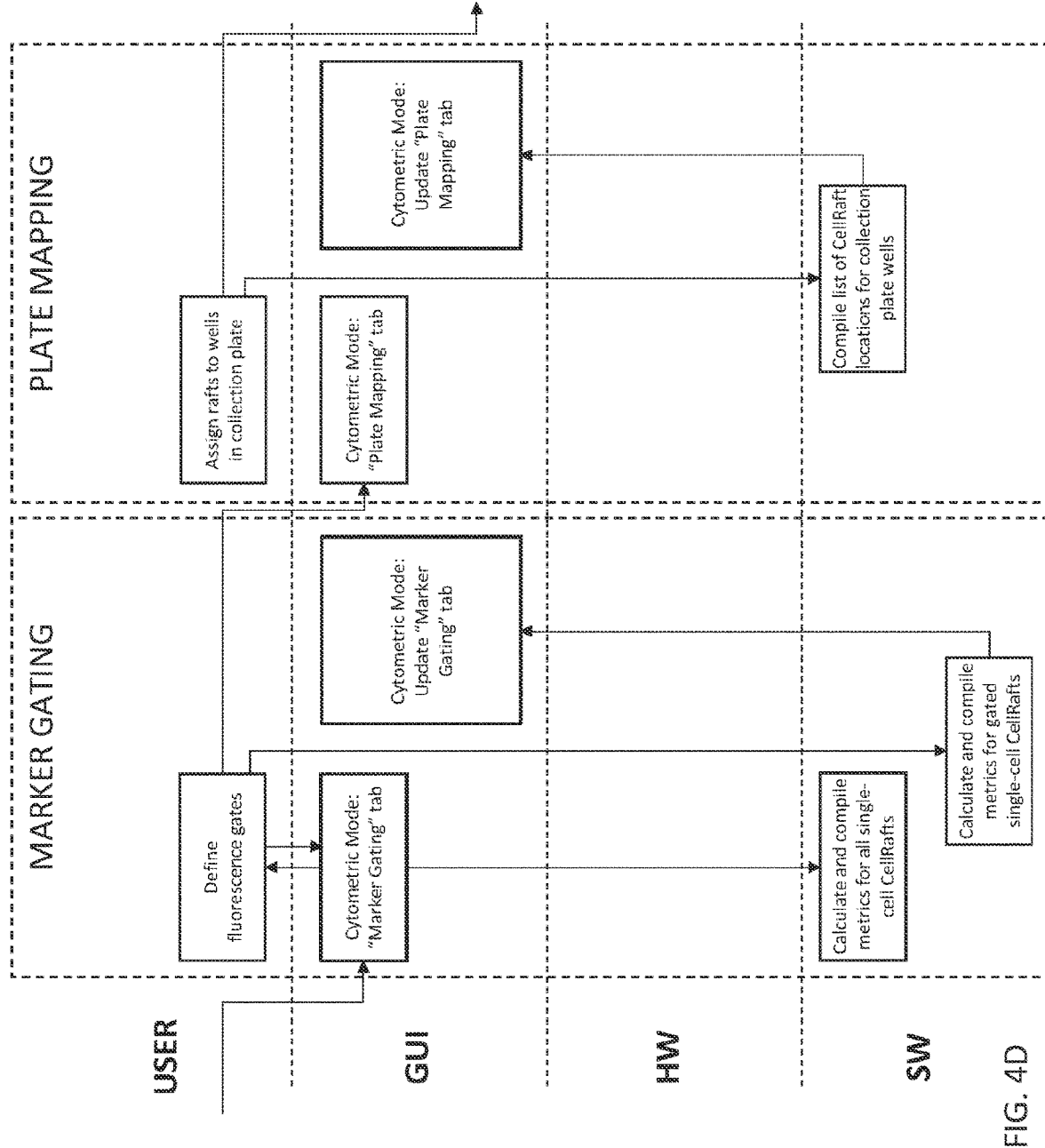

FIG. 4D illustrates the next stage of the example experiment if the user 108 selected the cytometric mode, marker gating and plate mapping. During marker gating, the GUI 126 presents a screen for the user 108 to specify marker gating parameters. The user 108 defines fluorescence gates. For example, the user 108 can specify a threshold color intensity. The controller 124 calculates and compiles metrics for gated single-cell rafts, and the GUI 126 presents a screen displaying results.

A marker is a cellular feature, which may be represented by a nucleic acid, a protein, other type of organic or inorganic molecule, or cellular feature such as morphological characteristics and organellar size and structure, the detection of which within a given cell is used to identify or classify a given cell, or to distinguish it from other types of cells which may not contain the given marker or contain it to a different degree. The presence, relative amount or quantitative amount of a marker can be detected using a range of methods and materials. These include using dyes, including fluorescent dyes, which label cells, organelles or other cellular features such as cytosekelton, nucleus, mitochondria and a range of other organellar compartments. Such dyes are well known in the art. They may also include using methods and materials for detecting native molecules with an optically detectable probe which may be represented by a nucleic acid with complementary sequence to the marker sequence, an antibody against a specific marker protein or transgenic approach where a gene expressing the marker is engineered to include a non-native moiety such as a fluorescent motif (green fluorescent protein, for example), antigen (HisX6 for example) or enzymatic activity (luciferase or alkaline phosphatase, for example).

In the context of this specification, a marker may also be a fluorescent dye, alone or in combination with one or more chemical or affinity moieties, that may be used to determine whether a cell is present, or whether a given cell is dead, alive, intact, not intact, or any other cellular condition or process. The term marker may also be used herein to describe the signal, such as a fluorescence or other optically detectable signal, that is detected by image analysis in the automated system and used to identify or classify a given cell or to distinguish it from other types of cells or cells having different characteristics or features.

During plate mapping, the GUI 126 presents a screen for assigning cell rafts to wells in the collection plate 114. For example, the user 108 can manually select cell rafts from a graphical display of cell rafts and assign cell rafts to a graphical display of wells in the collection plate 114. In another example, the controller 124 can randomly assign cell rafts to available wells in the collection plate 114. The controller 124 can select cell rafts based on user-specified criteria, e.g., by selecting each cell raft that is both determined to be a single-cell raft (e.g., with at least a specified level of confidence) and has a specified marker present (e.g., the detected marker is present at least at a threshold level). The controller 124 compiles a list of cell raft locations for collection plate wells.

In some examples, the GUI 126 displays, for all cell rafts within a currently selected marker gate, the approximate positions of the cell rafts on the microwell array 112 and a 2D histogram, or scatterplot, of fluorescence intensities within one or two of the imaging channels. Each cell raft within the gated population is represented on the scatterplot by a distinct visual indicator (e.g., a single yellow filled circle), whose (x,y) position is equal to the fluorescence intensity of the cell raft within the respective imaging channels corresponding to the two axes. Fluorescence intensities are integrated across the entire cell raft and are scaled relative to the maximum integrated cell raft intensity within the overall single-cell resident population for that imaging channel. Other indicators, e.g., colored flags, along each axis allow the user 108 to easily switch the imaging channel for a given axis.

In some examples, the GUI 126 can provide user interface controls that allow the user 108 to create marker gates on a fluorescence intensity scatterplot:

QUADRANT—A single left-click on the scatterplot defines the position of a set of cross-hairs. A double-click within any of the four quadrants defined by the cross-hairs creates a new gate for that quadrant. Each of the quadrants can be used to create separate gates.

LINE—Two left-clicks on the scatterplot define the trajectory of an infinite line across the scatterplot. A double-click on either side of the line creates a new gate. Both sides of the line can be used to create separate gates.

ELLIPSE—A first left-click on the scatterplot defines the center of an ellipse. A second mouse-click defines one axis and radius of the ellipse relative to the center. A third mouse-click defines the orthogonal radius relative to the first axis. A double left-click inside the ellipse creates a new gate. Given the methodology for defining the ellipse, the ellipse may extend beyond the range of the scatterplot.

POLYGON—Successive left-clicks on the scatterplot define the vertices of a polygon. To close the polygon, left-click on the original vertex. There is no limit on the number of vertices that can be defined, though the edges of the polygon cannot cross one another. A double left-click inside the polygon creates a new gate.

In some examples, the system 100 will allow the user 108 to define multiple ellipses and polygons on a single 2D scatterplot. If such gates overlap, when the user selects the overlapping region, the new gate is created from the original gate geometry. In some examples, when a previously created marker gate (parent gate) is selected as the current marker gate, the GUI 126 only displays the cell rafts within the selected gate on the scatterplot and array schematic. Consequently, when a new marker gate geometry is drawn on the scatterplot and used to create a new marker gate (child gate), only the cell rafts within the parent marker gate are screened for inclusion into the child gate, despite the fact that additional cell rafts within the overall single-cell resident population may fall within the child gate geometry.

Figure 4E:
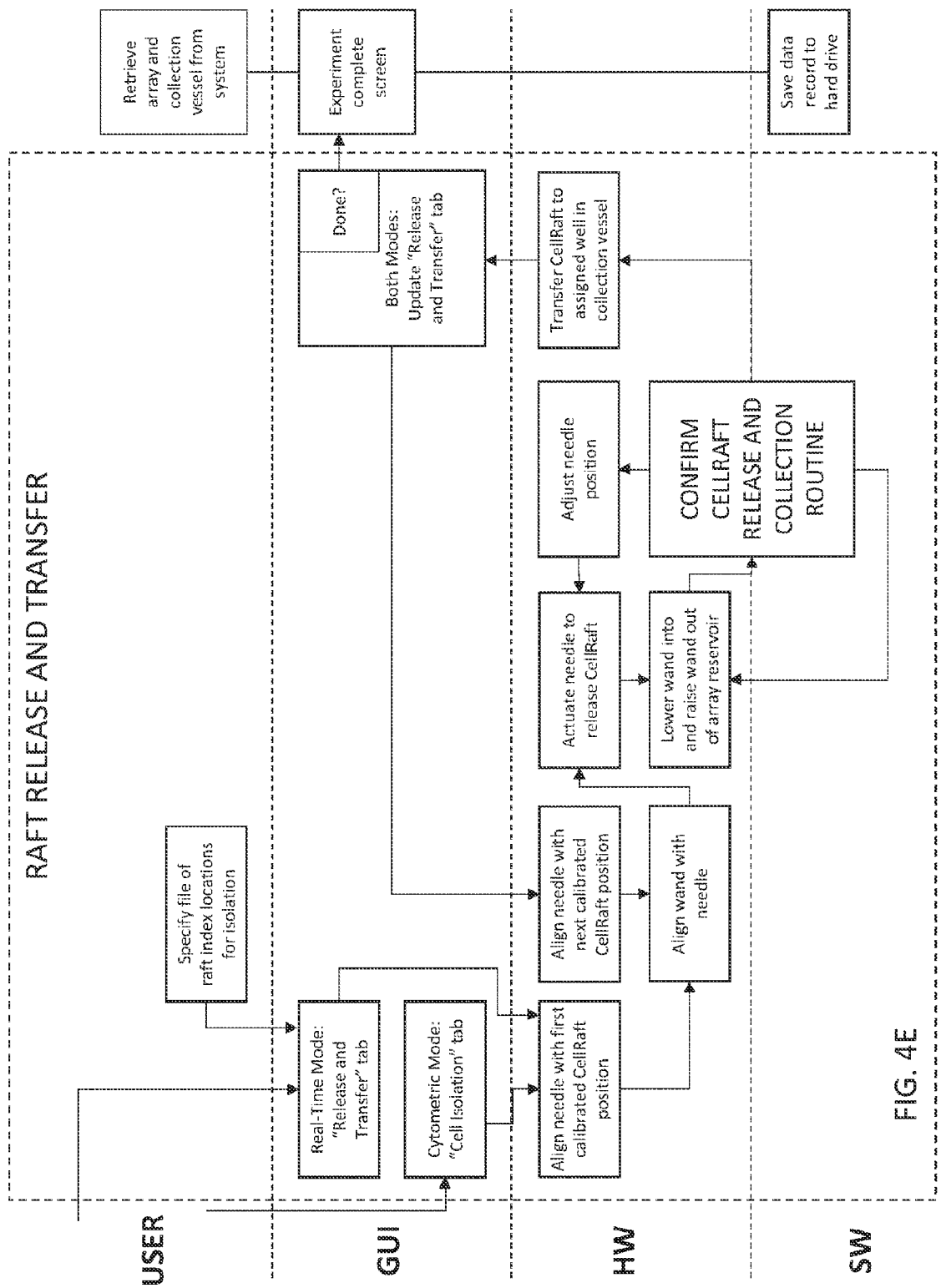

FIG. 4E illustrates the next stage of the example experiment, raft release and transfer. The selected cell rafts are released from the microwell array 112 and transferred to mapped locations on the collection plate 114. The instrument assembly 104, under control of the controller 124, aligns the release probe 154 with the first calibrated cell raft position and aligns the magnetic wand 162 with the release probe 154. Then, the instrument assembly 104 actuates the release probe 154 to release the cell raft, lowers the magnetic wand 162 into the microwell array 112, and then raises the wand away from the microwell array 112.

The controller 124 executes a confirm cell raft release and collection routine. For example, after releasing the cell raft, the controller 124 can move the XY stage 148 to image the cell raft that was released. The controller 124 can then perform image analysis on the obtained image to determine whether or not the cell raft is depicted in the captured image. If the cell raft is not depicted, then the controller 124 can confirm release. If the cell raft is depicted, then the controller 124 can repeat the release routine with the release probe 154, e.g., a specified number of times until stopping to report an error.

After confirming release, the controller 124 transfers the released cell raft to the assigned well for that cell raft in the collection plate 114. The GUI 126 can update a status screen depicting, e.g., the cell rafts that have been released and the cell rafts remaining for release. The controller 124 then selects another cell raft for release, aligns the release probe 154, actuates the release probe 154, and then controls the magnetic wand 162 to collect the released cell raft.

The controller 124 repeats the process for each cell raft that has been selected for release. When each of the cell rafts selected for release has been transferred, the GUI 126 presents a screen indicating completion. The user 108 retrieves the microwell array 112 and the collection plate from the system.

The user 108 can use the GUI 126 to save a summary file, e.g., to a local hard drive. The summary file may be compatible with any suitable database structure and typically includes data on: 1) imaging channel used for cell identification; 2) imaging channels used for cytometric analysis; 3) description of the selected marker's fluorescence signal gates used for cytometric channels (e.g., center point of circle and radius) 4) exposure time used for each imaging channel; 5) total scan time (if performed); 6) position of the single-cell raft in the microwell array 112 that is assigned to each well of the collection plate 114; 7) mean fluorescence signal intensity (in relative fluorescence units—RFUs) in each imaging channel for each collected cell raft; and 8) date and time of day run was performed when the user 108 acknowledged placing the microwell array 112 on the system. The controller 124 can export images from all active imaging channels selected by the user 108 for each retrieved and collected single-cell rafts in a standard image file format compatible with the image.

Figure 5:
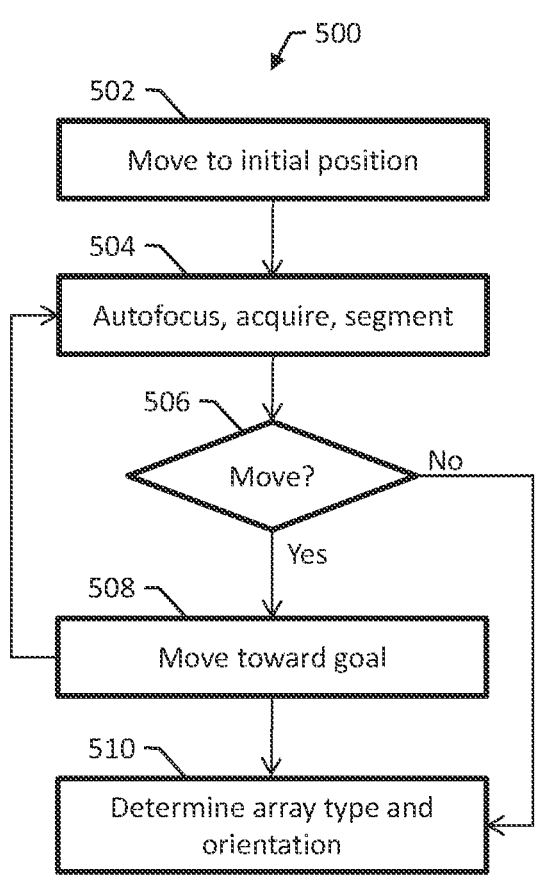
FIG. 5 is a flow diagram of an example method for determining an array position and type for a microwell array.

FIG. 5 is a flow chart of an example method 500 for determining an array position and type for a microwell array. The method 500 can be performed by the controller 124 of FIG. 1 and will be described with respect to the system 100 of FIG. 1. In general, the method 500 includes searching for a specified position (e.g., a corner) of the microwell array 112 in an automated manner using, e.g., known array geometry, manufacturing tolerances, and cell rafts detected in images.

The method 500 includes moving the XY stage 148 to an initial position (502), e.g., an estimated position for imaging one of the corners of the microwell array 112. The method 500 includes autofocusing the microscope system, executing an image acquisition routine, and segmenting the obtained image to determine locations of cell rafts within the obtained image (504). The method 500 can include calculating an average cell raft size, e.g., for a square cell raft, the length of the sides (L).

The method 500 includes determining whether to move the XY stage 148 to locate a corner of the microwell array 112 (506), e.g., determining whether a corner is depicted in the obtained image. For example, if one or more cell rafts are detected within a threshold distance (e.g., a distance 2*L) of the top of the image, the method 500 can include determining to translate towards the top (e.g., by a distance L); and if one or more cell rafts are detected within a threshold distance of the left side of the image, the method 500 can include determining to translate towards the left (e.g., by a distance L).

If moving the XY stage 148, the method includes moving the XY stage 148 to move closer to a corner of the microwell array 112 (508) and repeating the search for a corner of the microwell array 112. When the corner is found, the method 500 includes 510 optionally moving the XY stage 148 into a final position based on the location of the corner for determining the array type and orientation and autofocusing and obtaining an image at the final position.

The method 500 includes determining the array type and orientation based on the image at the final position (512). For example, the array type can be coded into the microwell array 112 by coding a pattern into a specified corner (e.g., top-left corner) of the microwell array 112. Cell rafts can provide digital information by being present or absent (i.e., so that microwells are filled or unfilled). The method 500 includes determining whether to image additional areas of the microwell 112 to determine the type and orientation (514). For example, the method 500 can repeat for each of four corners of the microwell array 112.

Figure 6:
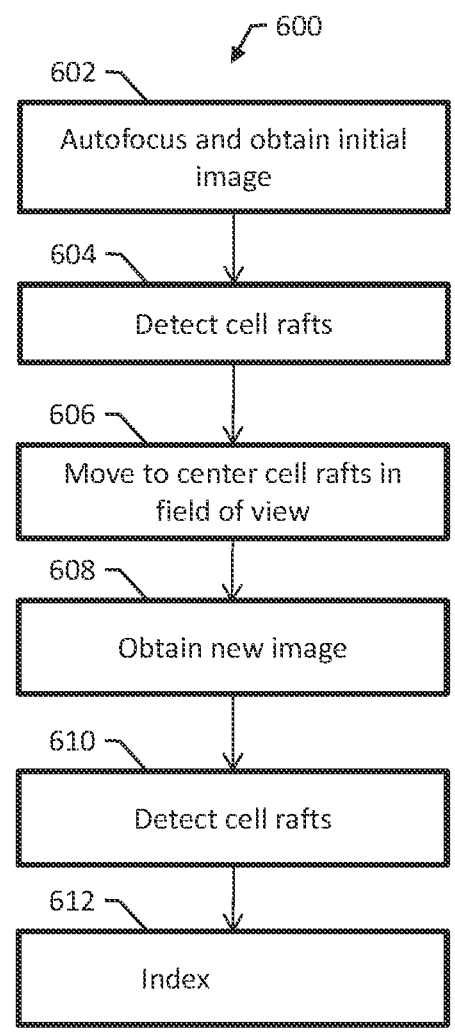
FIG. 6 is a flow diagram of an example method for navigating a microwell array.

FIG. 6 is a flow chart of an example method 600 for an autofocus and navigation routine. The method 600 can be performed by the controller 124 of FIG. 1 and will be described with respect to the system 100 of FIG. 1.

The method 600 includes, at a particular field of view of the microwell array 112, autofocusing and obtaining an initial image (602). The method 600 includes detecting cell rafts within the initial image (604). The method 600 includes moving the XY stage 148 to maximize the number of cell rafts in the field of view (606). For example, if the cell rafts are askew in the initial image, moving the XY stage 148 can include moving the XY stage 148 to center the cell rafts with the boundaries of the field of view. The method 600 includes obtaining a new image after the movement (608). The method 600 includes detecting cell rafts in the new image (610). The method 600 includes indexing the cell rafts in the new image (612), e.g., by assigning addresses to each cell raft detected in the new image. The addresses can be, e.g., row and column addresses.

For example, the following process can be performed with each increment in the field of view while imaging the microwell array 112:

1. The autofocus routine is executed and the brightfield image with the best autofocus score within the stack of images is selected for segmentation.
2. Using an OpenCV routine, the Otsu method is used to calculate the two pixel-intensity thresholds that maximize the inter-class variance across the three classes of pixels within the image. The upper threshold only is applied to convert the brightfield grayscale image to a binary image.
3. Using OpenCV routines, bounding boxes for each unique detected object, i.e. set of contiguous bright pixels, are calculated.
4. The bounding boxes are subsequently bandpass filtered to eliminate any object whose area deviates by more than 15% from the nominal cell raft area; and since cell rafts are nominally square, objects are also eliminated whose X and Y dimensions deviate by more than 10% from one another.
5. The cell raft row containing the most cell raft objects is selected to determine the skew of the array within the field of view. A first-order polynomial is calculated using a linear regression to the centers of the cell raft bounding boxes and the slope dictates the skew direction.
6. The four corner cell raft objects are selected, and based on the skew direction, their bounding boxes are used to calculate the margin between the cell rafts and the edges of the field of view.
7. The XY stage is moved to center the nominal cell raft sub-array within the field of view and the Z focus drive is adjusted to the point of best focus interpolated during the autofocus routine.
8. A new brightfield image is acquired and steps 2-4 are repeated.
9. The segmented cell rafts are sorted by row and column and appropriately indexed based on the indices assigned to the previous field of view and the translation direction of the XY stage.

FIG. 7A is a flow chart of an example method 700 for autofocusing a microscope objective. The method 700 can be performed by the controller 124 of FIG. 1 and will be described with respect to the system 100 of FIG. 1.

In some examples, the system 100 performs a rough autofocus function at the beginning of an experiment and then a fine autofocus function with every shift in the field of view of the imaging microscope. The first autofocus procedure for a given experimental run is performed after the microwell array 112 is loaded and the system begins initialization. A system configuration file can specify the X and Y positions for the XY stage 148 that align the microscope objective and system field of view with the upper-left quadrant of a single-reservoir microwell array or the upper-left reservoir of a quad-reservoir microwell array. The system navigates to that position and performs a rough autofocus procedure as follows:

1. The focus drive is moved to the minimum position in the focus search range as defined in the configuration file.
2. A brightfield image is acquired using, e.g., 2× binning and a dynamically determined exposure time.
3. In parallel:
   a. The image data is transferred from the camera and a focus score is calculated that quantifies the image contrast based on the variance in pixel intensities across the image.
   b. The focus drive is moved up, e.g., 100 μm.
4. If the focus drive has not reached the top of the search range as defined in the configuration file, repeat steps 2 and 3. If it has, the software extracts the focus position with maximum focus score.

The system 100 can then autofocus the microscope objective at a particular field of view using any appropriate technique. For example, the controller 124 can execute a Z-stack routine to search for an autofocused position on the Z axis. The Z-stack routine selects bottom and top search limits along the Z axis and a fixed step size between sample focus positions. In some examples, during an array scan, the search limits can apply for every field of view within the microwell array 112. The Z-stack routine then acquires an image and calculates a focus score at each sample focus position and then either extracts the position with the best focus score or interpolates a best focus position based on the sample focus positions. Other examples of search routines include the golden search method and Brent's method.

The method 700 illustrated in FIG. 7 can be considered a modification to a Z-stack routine to leverage information gained from neighboring fields of view. The method 700 can be useful, e.g., during an array scan, so that search limits can potentially be narrowed to improve the speed or the accuracy or both of autofocusing.

The method 700 includes moving the XY stage 148 to a new field of view and moving the microscope objective, along the Z axis, to an end point (e.g., bottom or top) of a possible focus range (702). In some examples, the method 700 includes determining, if available, the possible focus range (or otherwise determining a number of sample focus positions) based on focus positions from at least one neighboring field of view of the microwell array 112.

For instance, focus positions from neighboring fields of view are not typically available at the beginning of an array scan, but typically would be available as the scan progresses. In some examples, the method 700 includes selecting top and bottom search limits along the Z axis and step size between sample focus positions based on an average of any focus positions already determined within eight neighboring fields of view. FIG. 7B illustrates a range of sample focus positions along the Z axis.

The method 700 includes acquiring, using the camera 140, an image at a sample focus position (704). The method 700 includes moving the microscope objective, along the Z axis, the microscope objective to a next sample focus position (706), e.g., by moving the microscope objective up in a fixed step size such as 28 microns. In method 700 includes, transferring the image data to the computer system 102 (708) and calculating a focus score for the image (710). Any appropriate type of quantitative focus metric can be used for the focus score, e.g., the focus score can be determined based on a gray-level variance.

The method 700 can optionally include calculating the focus score in parallel with moving the microscope objective to the next sample focus position. The method 700 includes waiting (712), if needed, for both operations to complete. The method 700 includes determining whether there are more sampling focus positions to sample (714), e.g., whether the microscope objective is at the top (or bottom) of the possible focus range. If there are more sampling focus positions to sample, the method 700 repeats imaging and calculating a focus score for the next positions.

The method 700 includes interpolating the Z axis position of best focus using the Z locations of the sample focus points and the focus scores at the sample focus points (716). FIG. 7C illustrates an example plot of sample focus positions (on the horizontal axis) and focus scores (on the vertical axis). For example, the method 700 can include extracting the Z axis position of the sample focus point with the best focus score ($Z_1$, $FS_1$ in FIG. 7C) and the two sample focus points on either side (along the Z axis) of that sample focus point ($Z_2$, $FS_2$ and $Z_3$, $FS_3$ in FIG. 7C). Then the interpolated Z axis position ($Z_{focus}$) can be calculated as follows:

$$Z_{focus} = Z_1 + \text{SIGN}(Z_2 - Z_3)\left(\frac{FS_2 - FS_3}{FS_1 - FS_3}\right)\left(\frac{Z_{step}}{2}\right)$$

The SIGN operator yields a positive or negative sign depending on the difference between the Z axis positions of $Z_2$ and $Z_3$, and $Z_{step}$ is the step size between sample focus positions. The interpolated focus position can then be used for any appropriate imaging for the system 100.

Although the system 100 is described as autofocusing at each field of view, the system 100 can, in general, use any appropriate technique for focusing the microscope objective. For example, the system can perform an interpolation of a focus plane at any array position within the array by fitting a surface to the subset of focal planes measured versus (x,y) positions within the array. Surface fitting can be based on, e.g., a model derived from physical properties of the array (dimensions, elasticity, etc.) and the weight of the fluid within the reservoir. For example, the system 100 can use a thin-plate spline, which: calculates a minimally bended (i.e. minimal second derivatives) smooth surface that represents a least-squares minimization between the surface and the control points; uses a radial basis function $U(r)=r^2 \ln(r)$ between the control points; and uses an L-U decomposition to calculate the second-order polynomial weights and first-order coefficients for the surface as a function of (x,y).

Figure 8:
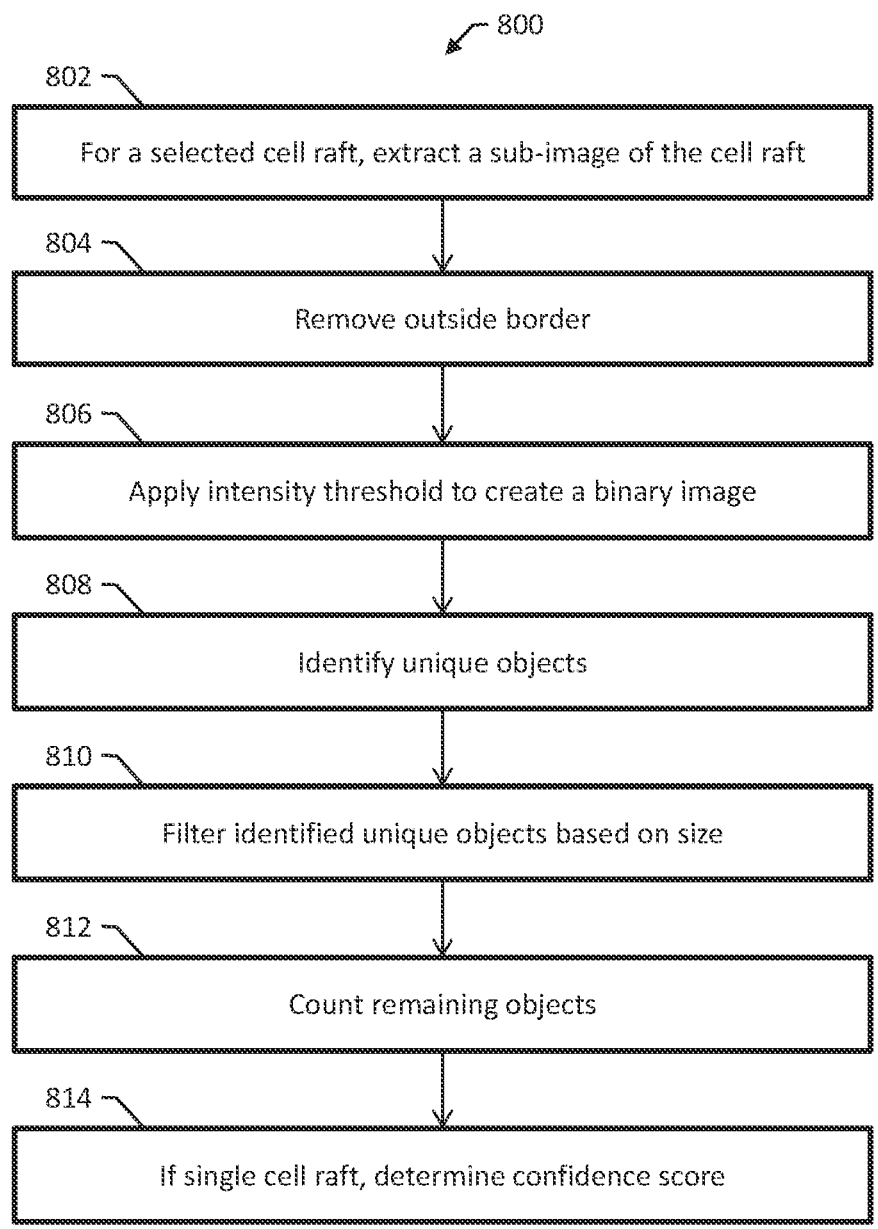
FIG. 8 is a flow diagram of an example method for identifying single-cell rafts in a microwell array.

FIG. 8 is a flow chart of an example method 800 for identifying single-cell rafts in a microwell array. The method 800 can be performed by the controller 124 of FIG. 1 and will be described with respect to the system 100 of FIG. 1.

The method 800 includes, for a selected cell raft, extracting a sub-image of the cell raft (802). The method 800 includes removing an outside border of the image (804) (e.g., by masking) and applying an intensity threshold (e.g., a user-specified threshold) to the image to create a binary image (806).

The method 800 includes identifying unique objects within the binary image, e.g., using any appropriate object detection algorithm (808). The method 800 includes filtering the identified unique objects based on size (810), e.g., by discarding identified unique objects having fewer than a threshold number of pixels (e.g., 10 pixels). The method 800 includes counting the remaining objects after filtering (812) and identifying the selected cell raft if only a single cell is depicted.

The method 800 optionally includes determining, if the selected cell raft is identified as a single-cell raft, a confidence score indicating a degree of confidence in the determination that the selected cell raft is a single-cell raft (814). For example, the selected cell raft can be further processed using its fluorescence morphology to assign a confidence level to the single-cell classification. For each candidate single-cell cell raft:

Local maxima within the grayscale pattern of the detected fluorescence object are identified using a combination smoothing and dilation process:
A 9×9 flat structuring element (SE) is defined with a zero at its origin.
Using SE, a grayscale dilation is applied to the masked image (I): GD=I ⊠ SE
The zero at the origin of the structuring element has the effect that the grayscale intensity of GD equals the intensity of I at positions of maximum intensity within I over a 9×9 local region.

The masked image (I) is subtracted from the dilated image (GD):

$$SI(x,y)=GD(x,y)-I(x,y)$$

Elements within SI(x,y) equal to zero represent local maxima within the original masked image I(x,y).

The local maxima are analyzed to determine a confidence score that the object corresponds to a single nucleus. The cell raft starts with a rating of HIGH confidence. For every combination of two detected local maxima within the grayscale image of the fluorescent object:
  The pixel intensities along a line between the two local maxima are compared against a theoretical linear gradient between them. If the actual intensity dips below 75% of the linear gradient at any point along the line, the cell raft is demerited by one level (from HIGH to MEDIUM, MEDIUM to LOW, or LOW to removal from the candidate list). If the intensity dips below 50% of the linear gradient, the cell raft is demerited by two levels. (NOTE: the demerits are cumulative over all combinations of identified local maxima.)
  As a measure of circularity of the object, the distance between the two maxima (D) is compared to their respective distances ($DT_1$, $DT_2$) from the edge of the detected object (as measured by the distance transform value applied to the complement of the thresholded image).
    If $2*D>(DT_1+DT_2)^2$, the cell raft is removed from the single-cell candidate list.

In some examples, any cell raft candidates remaining after the culling process are classified according to their confidence level and available for filtering based on confidence rating, size, or maximum intensity before inclusion in the preliminary single-cell population for marker gating.

In general, the controller 124 can use any appropriate image analysis techniques for identifying single-cell rafts. In some examples, the controller 124 can, for a sub-image of a cell raft, threshold the sub-image; if the number of discrete objections is one after thresholding, calculate a distance transform of a complement of the thresholded image; create a negative of the distance transform; set background pixels to −Inf (or other appropriate placeholder value); identify and mark local minima to differentiate a single cell from a cluster of cells; and perform a watershed transform to draw boundaries around cells.

Figure 9:
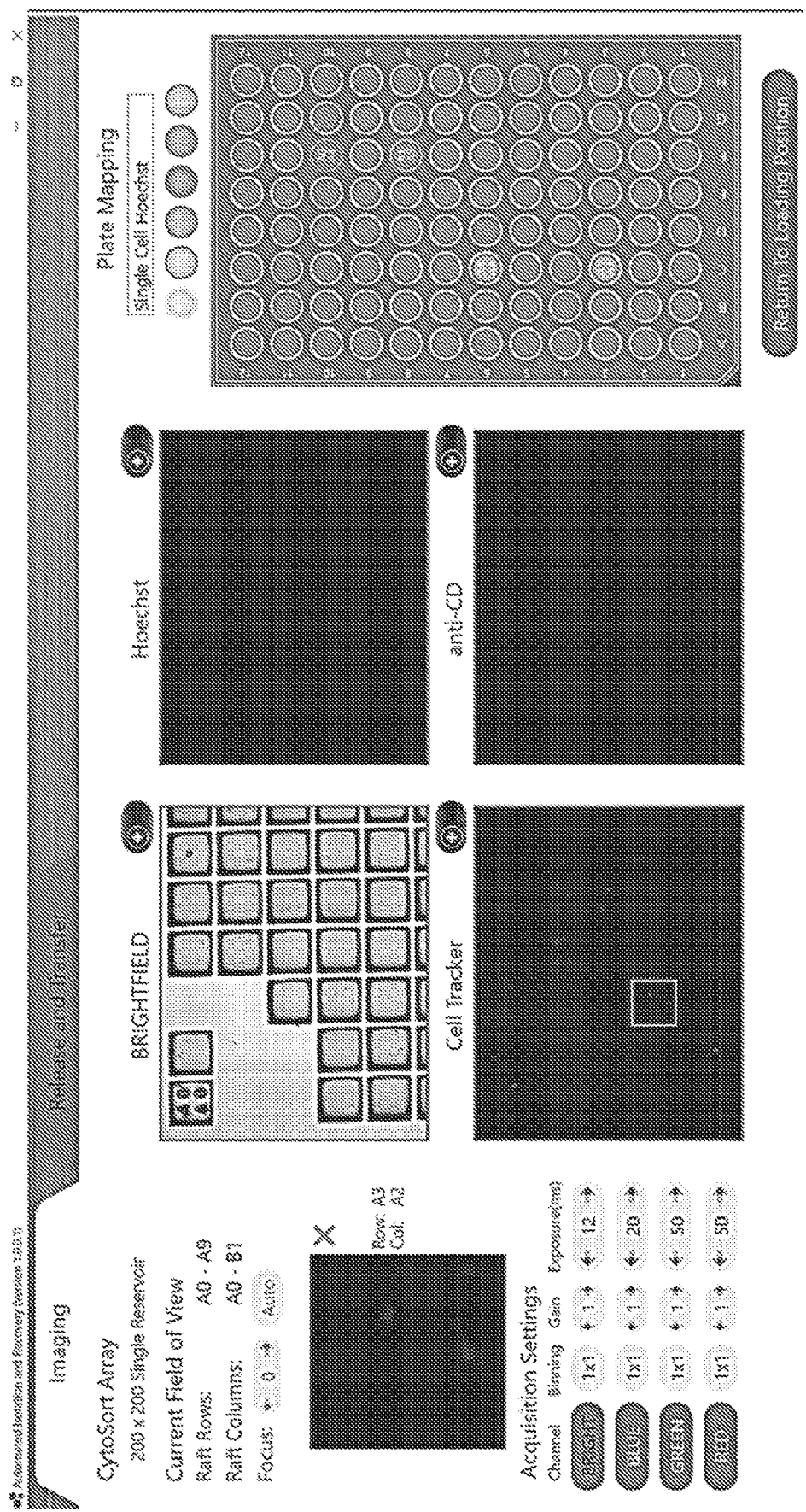
FIG. 9 is a screen shot of an example screen of a graphical user interface for selecting cells rafts and mapping a collection plate.

FIG. 9 is a screen shot of an example screen of a graphical user interface for selecting cells rafts and mapping a collection plate, e.g., for a real-time imaging mode as described above with reference to FIG. 3A. FIG. 9 illustrates an example "Imaging" screen GUI (e.g., from the GUI 126 of FIG. 1) that combines multiple elements of system control and sample capture. The user interface further provides user interface controls that allow the user to move the field of view in each direction or move to any position with a single mouse click, as well as to allow the user to adjust the focus of the imaging optics or initiate autofocus. The user interface further allows the user to turn on or off the brightfield and red, green, and blue fluorescent channels, set the exposure time and gain for each fluorescent channel, the binning for each fluorescent channel, and allow the user to adjust the exposure time independently for each active imaging channel.

As shown in FIG. 9, the user can click on or select a raft of interest within any of the images, inspect a zoomed image of the raft, and select a particular raft for isolation. The user interface indicates to the user the position of the currently displayed field of view on the microwell array. The GUI screen also displays a map of the collection plate (96-well format shown as an example) and permits the user to assign the single-cell raft selected for isolation to a specific position within the collection plate specified at the beginning of the experiment.

Using display elements from FIG. 9, the GUI can also produce a screen that can be used to monitor the release and transfer process. The GUI screen can display the list of rafts selected for isolation, allow the user to initiate the isolation process via raft release from the microwell array, to transfer rafts to the collection plate via the magnetic wand, and to track the progress of the isolation process by displaying time to completion and each deposit in the collection plate map.

When using the system 100 in cytometric image analysis mode, an "Imaging" tab GUI containing elements similar to FIG. 9 can be displayed, allowing the user to navigate the system field of view within the microwell array and visualize real-time images and pixel histograms for the purposes of setting the imaging parameters for the three fluorescence imaging channels to be used during the full automated scan of the microwell array. An "array scanning" tab GUI within the cytometric image analysis mode can be displayed that allows the user to initiate a full scan of the microwell array, track the progress of the scan, and pause/resume the full automated scan of the microwell array. The GUI displays the position of the current field of view within the array as well as the images acquired from that field of view.

Figure 10:
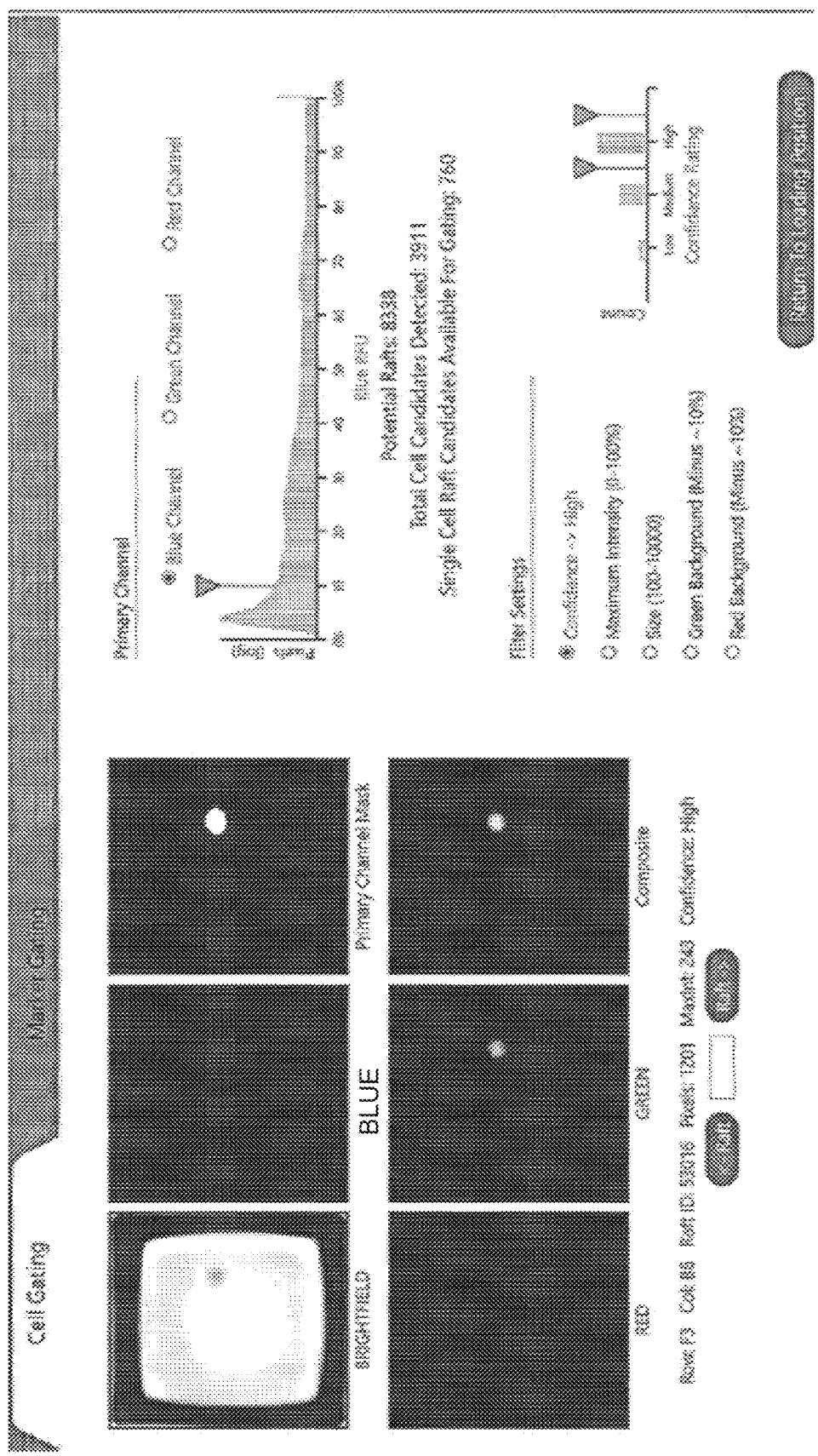
FIG. 10 is a screen shot of another example screen of the graphical user interface.

FIG. 10 is a screen shot of another example screen of the graphical user interface. FIG. 10 illustrates a "Cell Gating" or cell identification tab GUI within the cytometric image analysis mode. The Cell Gating tab GUI allows the user to set the parameters by which fluorescent objects within the primary imaging channel are segmented to determine the number of cells on each raft within the array. The controls allow the user to set the intensity threshold for the object segmentation, review the effects of the setting change on the segmentation, and apply various filters within the population of single-cell rafts to further screen candidate rafts from the population. These settings can be applied to the method 800 for single cell detection so that the user can optimize the system's identification of single-cell rafts with greater than 95% efficiency. The user interface displays a histogram of signals for the "Cell Identification" channel with the X direction representing pixel intensity and the Y axis representing the number of pixels within the full array scan at a given signal intensity. A user can use a mouse to set an indicator of the current single cell gating threshold on the histogram.

The user interface allows the user to change the single cell gating threshold to a value representing a normalized percentile calculated as a function of both minimum (0%) and maximum pixel intensity (100%) detected during the full array scan, as well as a confidence interval for the single cell count on the array. The GUI screen will also indicate to the user the total number of rafts identified as containing cells during the full array scan of the microwell array, and the number of single cell-resident rafts which meet the user-specified threshold parameters for subsequent isolation.

The user interface can display a "Marker Gating" tab within the cytometric image analysis mode. After completing the cell gating processes, an additional screen in the user interface will display an image of the full microwell array with the positions highlighted where single cell-resident rafts are located and the total number of single cell-resident rafts found on the array. The user interface screen can also display a 2D histogram, providing a single point representing each single-cell raft, plotted along the X and Y axis for each of two cytometric marker channels specified by the user. The interface can further provide user interface controls that allow the user to apply cytometric marker gates on the histogram in any any appropriate format, e.g., as described above with reference to FIG. 4D.

The user interface also allows the user to use a mouse to click the positions of single cell-resident rafts within the full image of the microwell array or on the 2D scatter plot, as well as to view images of the selected single-cell raft in all active fluorescent channels and brightfield. The interface further allows (e.g., in the real-time imaging mode) the user to randomly select single-cell rafts in all active fluorescent channels and brightfield. Using a plate mapping display similar to the plate mapping display shown in FIG. 9, the user can assign the selected single-cell raft to a specific position within the collection plate specified at the beginning of the experiment.

The systems and methods described in this specification are applicable to many problems in cell biology where a cellular process is monitored through a time varying fluorescence signature. The effect of specific transgenes, siRNA or small molecules on cellular proliferation or survival could readily be monitored in model cell systems, and cells displaying unusual properties such as extreme gene expression, cell proliferation or extended survival could be isolated for expansion and more detailed study. In the field of cancer biology, the system could also be used in primary human tumors, which contain diverse cell populations, to isolate and study individual cells with unique temporal characteristics.

For example, a time-course analysis can be accomplished using the functionality inherent within the cytometric image analysis mode. In the case of an application involving a drug or reagent challenge, a full array scan can be performed at $t=t_1$—before the addition of a drug or reagent—for the purposes of 1) identifying single-cell rafts within the array and 2) quantifying a baseline fluorescence level within one of the reporter fluorescence imaging channels. After the addition of the drug or reagent and sufficient incubation time, a second full array scan can be performed at $t=t_2$. The system can subsequently enable single-cell raft selection for isolation by calculating and displaying the difference in measured fluorescence between $t_1$ and $t_2$ and by allowing the user to create gates based on that difference.

Various permutations are possible for this workflow where a fluorescence value is compared between two different time points. If the two time points are minutes or hours apart, the cells may be left inside the instrument. If the two time points are many hours or days apart, then the microwell array containing the cells can be removed from the instrument between imaging runs and placed in a standard cell culture incubator.

An additional application for two-point time-course analysis is the evaluation of clonal colony propagation during a transfection experiment with a fluorescent reporter gene. The preliminary scan would identify single-cell rafts which are required for a clonal colony. The secondary scan would allow evaluation of total colony fluorescence, indicative of overall colony size and efficacy of the transfection within the colony.

To take the time-course capability further, the system can perform any number of additional array scans at times $t=t_3$, $t_4, \ldots, t_N$, quantify the fluorescence intensity within the reporter imaging channel, and display plots of measured intensity versus time. In addition to creating single-cell raft population gates based on single-time-point fluorescence intensities or intensity changes between two time points as previously described, the software can further enable the user to create gates based on the shapes of the fluorescence time curves. Curve shape based gating capability can be facilitated using dimensionality reduction, clustering, and classification techniques such as principal component analysis, Fourier transforms, wavelet transforms, hierarchical cluster analysis, or linear discriminant analysis.

While fluorescent intensity is an excellent measurement of the abundance of an analyte within a single cell, there is also potential to use this capability to examine the localization of an analyte within a given cell. For example, many membrane proteins respond to a given ligand or other stimulus by internalization, typically through endocytosis, and translocating to other cellular compartments or organelles such as the nucleus. Analysis of proteins displaying this behavior may require not only monitoring fluorescent intensity, but also monitoring changes in the localization pattern of its fluorescent signal. In the case described above for example, comparing a protein's plasma membrane-linked signal to its nucleus-linked signal may provide an indication of overall signal transduction through a given pathway. Many types of analytes could take advantage of this method, including proteins, nucleic acids and organelles themselves such as endoplasmic reticulum, endosomes or mitochondria. Image analysis algorithms for these types of time course experiments would likely employ a segmentation-based method, identifying objects and imputing their geometry to predict the nature of the cellular compartment to which they are localized, or allowing the user to ascribe a specific fluorescent signal to a given cellular compartment.

FIGS. 11A-11I illustrate an example experiment where an automated, computer-controlled microwell release and collection system comprising an actuator, an imaging device, and a processor, including image processing and analysis algorithms is used with a microwell array to examine and isolate transfected K562 cells (a human myelogenous leukemia cell line). The cells were transfected using standard techniques with a single-stranded oligodeoxynucleotide repair template containing the leukemia-associated S34F mutation along with a plasmid containing genes encoding the Cas9 nuclease, an enhanced green fluorescent protein (EGFP) reporter gene, and one of two sgRNAs designed to bind to specific sequences in the U2AF1 gene. Cells were incubated at 37° C., 5% CO2 in 2 mL of pre-equilibrated culture medium for 24 hours following transfection. The transfected cells were then stained with 1 μM calcein AM or CellTracker Deep Red for 30 min, washed and imaged following the respective staining protocol and seeded onto microwell arrays. The cell rafts were immediately imaged to identify the position of cell rafts with a single cell. Cell rafts with greater than one cell were excluded from subsequent analyses. The arrays were then imaged every 12 h until 72 h post-transfection.

The components of the automated system where generally similar to the components of the system 100 of FIG. 1. The imaging device in the automated system comprised a MVX10 MacroView upright microscope (Olympus, Center Valley, Pa.) equipped with an ORCA-Flash4.0 CMOS camera (Hamamatsu, Bridgewater, N.J.) that was used to acquire bright field and fluorescence images. A plan apochromat objective lens (1× with numerical aperture of 0.25) paired with a magnification zoom enabled a wide range of effective magnifications (0.63×–6.3×) during imaging. The sample and objective movement was automated using a PS3H122

Motorized Focus Drive and a H138A motorized XY translational stage (Prior Scientific Inc., Rockland, Mass.). A Lambda 10-3 optical filter changer positioned an emission filter wheel (LB10-NWE), an excitation filter wheel with SmartShutter (LB10-NWIQ) and a stand-alone SmartShutter shutter (IQ25-SA) (Sutter Instrument, Novato, Calif.). A filter set (89000-ET-Sedat Quad; Chroma Technology Corp, Bellows Falls, Vt.) with 5 excitation bandpasses (350±50 nm, 402±15 nm, 490±20 nm, 555±25 nm, 645±30 nm) and 4 emission bandpasses (455±50 nm, 525±36 nm, 605±52 nm, 705±72 nm) permitted fluorescence measurement in the blue, green, red and far red wavelengths. An arc lamp (Lumen 200, Prior Scientific Inc., Rockland, Mass.) was used for illumination. All microscopy equipment was controlled by custom software written in MATLAB (MathWorks, Natick, Mass.) and used a Micro-Manager (Open Imaging, San Francisco, Calif.) core.

At varying times, brightfield and fluorescence images of the microwell array were acquired. An overlap of at least 300 µm (spacing between cell rafts+cell raft width) between imaged fields of view was used in all experiments to ensure full image coverage. For experiments to identify EGFP-expressing K562 cells, the cells were first stained with CellTracker Deep Red. Bright field and fluorescence images of the arrays were acquired 24 h to 72 h post-transfection at 12 h intervals.

A custom MATLAB program was used to control the microscope in the system for automated acquisition of bright field and fluorescence array images at designated time points and to process and analyze images. A graphical user interface (e.g., similar to the GUI 126 of FIG. 1) enabled user input, including fluorescence channel selection, camera exposure time, and microwell array geometry. The user interface was also used to direct the user to manually locate and focus on the 4 corners and center of the microwell array. The 5 identified points from each array were fit to a thin-plate spline in order to predict the position and focal plane for each field-of-view for the array based on interpolated planes from the fit based on the array dimensions.

At all magnifications, the cell rafts possessed high contrast borders under bright field illumination. The cell rafts were segmented and assigned array locations using the bright field images. Flat-field correction was performed on each bright field image to correct for uneven illumination intensity. Each bright field image was thresholded using Otsu's method and the pixels assigned a 1 or 0 based on their value above or below the threshold value. To remove debris on the arrays from consideration, binary images were further processed to fill the interior of each cell raft border and objects larger than 1.5× or smaller than 0.5× the known cell raft size were eliminated from analyses. Using this strategy, the positions of all cell rafts were identified at each time point and prior to cell raft isolation. Background noise was removed from fluorescence images by applying a top-hat filter. Otsu's method was then used to threshold each image and convert the image to binary. A watershed algorithm was applied to the binary image to separate cells in contact enabling the counting of fluorescent cells. The spatial resolution required for image acquisition was optimized by considering the pixel size, array image time, cell raft segmentation accuracy and cell identification success.

The release probe in the automated system consisted of two Delrin components: a motor housing for a small stepper linear actuator (20DAM10D2U-K; 15 mm travel; Portescap, West Chester, Pa.) and a needle mount. The needle mount possessed a clear polycarbonate window with a small hole through which a needle was secured. The clear, polycarbonate window permitted bright field microscopy with the needle in place. The linear actuator was controlled by a custom MATLAB program interfaced to an Arduino Uno (SparkFun Electronics, Boulder, Colo.) equipped with a motor shield (Adafruit Industries, New York, N.Y.). An automated mechanical system with customized software written in MATLAB was developed to release individual cell rafts when supplied with a target cell raft list by the imaging analysis software (e.g., similar to the system 100 of FIG. 1). A stepper linear actuator controlled the Z position of the release probe used to puncture the microwell array and dislodge the cell raft in an individual microwell. The release probe and motor were mounted beneath the microscope stage aligned with the optical path of the microscope objective. The user interface enabled the user to select the Z-travel distance during actuation for cell raft release. Cell rafts targeted for automated release were successfully dislodged with between 94 and 100 percent efficiency, depending on the number of times the release needle pierced the microwell array at the target location.

A motorized magnetic wand in the automated system was designed to capture, transfer, and deposit the superparamagnetic cell rafts into a collection vesicle. The retrieval wand was fabricated by placing a cylindrical NdFeB magnet (3.175 mm diameter, 25.4 mm length) within a hollow polycarbonate cylinder (4.76 mm outer diameter, 3.18 mm inner diameter, 63.5 mm length). The cylinder was blocked at both ends leaving the magnet able to move freely along the central axis of the cylinder. The retrieval wand was mounted to the microscope objective using Delrin components and its vertical movement controlled by a linear actuator (L12-30-50-06-R; Firgelli Technologies Inc., Victoria, BC, Canada, travel distance of 30 mm). The linear actuator was controlled by a custom MATLAB program interfacing with an Arduino Uno equipped with a motor shield. To capture cell rafts, the magnetic collection wand was placed in the medium above a microwell array within 2 mm of a released cell raft. Once removed from the array, the cell raft was held on the wand tip by a cylindrical magnet within the wand as well as the surface tension of the fluid droplet on the wand tip. Cell rafts were deposited into a 96-well plate with an efficiency of 100%.

Prior to recovering cell rafts from the array, the release needle location in the field of view was recorded. The X-Y-Z location of the collection wand relative to the array was also calibrated as well as its position relative to that of the wells in the 96-well plate. For cell raft release a selected cell raft was expelled from the microwell array by piercing the PDMS substrate with the needle using the cell raft release system. The magnetic collection wand was immersed into the array medium attracting the released magnetic cell raft. The collection wand then moved to and was immersed within a well of a nearby a 96-well plate containing culture medium. A NdFeB block magnet (101.6×76.2×6.35 mm) below the 96-well plate attracted the cell raft into the well. The block magnet was also positioned such that the cylindrical magnet in the collection wand was repelled by the block magnet.

A customized MATLAB program and user interface was used to integrate the actions of the various components of the system, allowing coordinated movement of the cell raft release probe during imaging, cell raft collection upon raft release and microscope stage movement to place collected cell rafts into a 96-well plate. Using the user interface, the user initiated a cell raft release, adjusting the travel distance until the needle just breaks through the PDMS. The user identifies the needle location, and the software stores the needle location in relation to the XY stage position. Next the GUI allows the user to manipulate the XY stage and cell raft collection system to place the wand tip into the 4 corners of the cell raft array and 4 corner wells of the 96-well plate. This information is then used to interpolate collection and deposition positions for each cell raft.

The automated system was used identify the position of cell rafts with a single cell and to track the duration and intensity of EGFP fluorescence of every cell. EGFP-positive cells were examined every 12 hours over a 72 hour period. Cell rafts that contained an EGFP-expressing cell at any time point were identified at the completion of the imaging time course by the image analysis software. A total of 220 cell rafts starting with a single cell contained at least one fluorescent cell during the imaging time, corresponding to a transfection efficiency of 1.9%. Cell rafts containing fluorescent cells were identified with 100% sensitivity, and the automated cell raft system was able to release cell rafts with >98% efficiency and collect cell rafts with 100% efficiency. The single-cell rafts were targeted for release and collection into 96-well plates. Cells that expanded into colonies were genetically analyzed to determine the presence of successful gene editing. Two K562 colonies were generated containing the S34F mutation in U2AF1, demonstrating the ability to sort cells based on the temporal evolution of fluorescent protein expression and providing selected cells and colonies that were successfully gene-edited.

The automated system also was used to analyze the temporal evolution of EGFP expression in transfected cells on the microwell array, and whether there were identifiable trends in EGFP expression that predicted whether a cell would proliferate after cell raft isolation. The mean fluorescence per cell obtained by the imaging system over 72 hours was used to categorize cells on individual cell rafts as low fluorescence for the entire duration, high fluorescence for the entire duration, low expression followed by high expression, and high expression followed by low expression. Cells that proliferated post-isolation were distributed stochastically throughout the four groups. There was no discernable difference in fluorescence expression at any single time point between the post-isolation proliferative and non-proliferative groups, and there was no correlation between proliferation of cells on the microwell array and proliferation after isolation of the cell raft. Analysis of the temporal evolution of EGFP expression also demonstrated that transfected K562 cells could take up to 72 hours to express EGFP following transfection. Furthermore, the automated system allows the user to correlate expression data taken over time on single-cell rafts in a microwell array with downstream molecular analysis, in this case a determination of successful gene editing in isolated clones derived from single cells assayed on a microwell array.

FIG. 11A shows a schematic of image processing and analysis used to identify and isolate cell rafts containing transfected K562 cells. FIG. 11B shows a raw brightfield image of a microwell array. FIG. 11C shows a bright field image of the same microwell array after a flat-field correction was applied. FIG. 11D illustrates that thresholding of the corrected image yielded a binary image marking the cell raft borders. FIG. 11E illustrates morphological filtering that was applied to fill in the cell rafts and remove any cell rafts touching the image border. FIG. 11F shows a fluorescence image of two touching cells loaded with calcein AM. FIG. 11G illustrates a top-hat filter that was applied to the fluorescence image to remove background noise. FIG. 11H shows that thresholding of the top-hat filtered image yielded a binary image with the two cells connected. FIG. 11I shows the results of applying a watershed algorithm to separate the touching cells.

In one embodiment of the invention, an automated, computer-controlled microwell release and collection system comprising an actuator, an imaging device, and a processor including image processing and analysis algorithms is used with a microwell array to examine the simultaneous measurement of T cell function with recovery of individual T cells.

An automated system (similar to the system 100 of FIG. 1) was used to measure, in a functional assay on the array, the ability of individual T cells to kill a population of target cells and to measure the time dependence of T cell mediated killing, or cytotoxicity, "on-array". They system was further used to viably sort specific cells into a 96-well plate for clonal populations that can be used as probes for monitoring antigen presentation under different situations and in different cell types.

A human T cell culture was generated against the influenza M1p antigen. Isolated peripheral blood mononuclear cells were used to obtain $CD8^+$ cells using standard methods. The cytotoxic T lymphocyte (CTL) culture was initiated by incubating the $CD8^+$ T cells with M1p pulsed DCs in CTS AIM V media with 10% human AB serum (complete media, CM) supplemented with IL-21. After a 3 d incubation, the cells were supplemented with CM plus IL-7 and IL-15 every 2 d. CTLs were restimulated with M1p-pulsed DCs 11 d after culture initiation in CM containing IL-21, IL-7 and IL-15. IL-2 was added 19 d after initiation of the culture. The CTLs were restimulated 21 and 34 d after culture initiation and were cryopreserved in aliquots 41 d after initiation of the culture. Cryopreserved CTLs were thawed and restimulated with M1p pulsed DCs. After 3 d, the CTLs were isolated using the $CD8^+$ T cell isolation kit and maintained in CM supplemented with IL-7, IL-15 and IL-2. $CD8^+$ T cells were plated on microwell arrays 2 to 3 d later. M1p/HLA-A*02:01 tetramer enumeration showed that 48.4% of $CD8^+$ T cells were specific for M1p. The bulk culture displayed antigen specific cytotoxicity against M1p pulsed autologous DCs compared to autologous DCs pulsed with the leukemia associated antigen PR1.

Dendritic cells (DCs) were differentiated from $CD34^+$ cells isolated from cryopreserved leukapheresis products obtained from the Hematopoietic Progenitor Cell Laboratory at UNC Hospitals using the CD34 Microbead Kit UltraPure (Miltenyi Biotec). $CD34^+$ cells were incubated for 12 d in CTS AIM V media with 10% human AB serum (complete media, CM), supplemented with GM-CSF, Flt3-ligand, SCF and IL-4 as described in the supplemental methods to yield immature DCs that were cryopreserved for future use. Immature DCs were differentiated into mature DCs by incubation with GM-CSF, IL-4 and TNF-a for 2 d and GM-CSF, IL-4, TNF-a, IFN-a and IL-6 for 2 d. Matured DCs were co-incubated with peptides (M1p or PR1) for at least 18 h.

Microwell arrays were coated in 0.1 wt % bovine gelatin in PBS and incubated at 37° C. for ≥2 h after which the gelatin solution was aspirated and the array was washed ×3 with PBS before plating cells.

The microwell arrays used for the analysis were comprised of a regular pattern (70×70) of cell rafts on which cells are cultured and assayed over time by microscopy. The cell rafts fabricated from a magnetic polystyrene possess a concave surface of 120 μm depth enhancing retention of cells on their surfaces during assay setup and performance. The microwell arrays were seeded with autologous DCs ("target") cells that had been pulsed with either M1p or PR1 peptides and labeled with Hoechst dye. Target cells were applied to the array in phenol-red free RPMI 1640 supplemented with human AB serum, penicillin, streptomycin and HEPES at a ratio of 30 cells per cell raft (147,000 cells per array). $CD8^+$ T cells were labeled with CellTracker Deep Red and placed onto the array at a cell:cell raft ratio of 1:1 in order to maximize the number of cell rafts that contained a single T cell. Cells settled onto the array in a stochastic manner so that the number in each well across the array followed the Poisson distribution, meaning that roughly ⅓ of the wells (36.8% or 1803 wells) are predicted to possess a single $CD8^+$ T cell, 26.4% (1294) are predicted to contain >1 T cell and 36.8% (1803) are expected to have 0 T cells. The media overlaying the array contained Sytox Green, a DNA binding dye that is membrane impermeable.

The assay was designed to identify cell rafts that contained a single T cell and showed a high rate of cytotoxicity against target cells as evidenced by increasing green fluorescence over a 6 h time course. Because both the target cells and T cells were applied to the media over the microwell array, individual cell rafts can have different numbers and ratios of target and T cells. Image acquisition, processing, and analysis was accomplished in a similar manner to that described above with reference to the system 100 of FIG. 1. Fluorescence images of the arrays were obtained every 30 min for 6 h while in the incubator housing the microscope and the development of green fluorescence over time was measured for each cell raft.

Fluorescence images were processed in a similar manner to the processing described above with reference to FIGS. 4A-4E. The fluorescence images were analyzed to determine the intensity, area, position and number of cells displaying each fluorophore (Hoechst, Sytox Green and CellTracker Deep Red). Top hat filtering and Otsu's thresholding was applied to each image to produce a binary mask of the cells on the microwell array. Within the mask created by each fluorophore, the intensity, location and number of pixels was recorded for each cell raft. A watershed algorithm was applied to each image in the far red channel (corresponding to cells stained with CellTracker Deep Red) to count the number of individual cells on each cell raft.

In parallel with the image acquisition, the MATLAB program processed and analyzed the acquired images. The MATLAB GUI was used to select the desired combination of bright field and fluorescence channels for imaging. The processing time of each set of images was faster than the microscope stage movement and image acquisition, so no additional time was added to the total scan time. The bright field images were used to identify individual cell raft locations. Due to the elastomeric nature of PDMS, image analysis was needed to accurately locate the exact positions of cell rafts on the array. The cell raft segmentation method included background estimation, flat-field correction, thresholding and morphological filtering. The vast majority of cell rafts (99.8±0.8%) were correctly identified without false positives (n=100 images, 100-121 cell rafts per image).

The analyses performed on the microwell arrays compared development of green fluorescence over time in cell rafts that contained either 0 or 1 $CD8^+$ T cell. Cell rafts with 0 T cells were considered the control and reflected the rate of spontaneous target cell death over the time of the investigation. A total magnification of 4× was used for scanning cell rafts, resulting in a pixel size of 1.62 µm/pixel. This magnification was chosen because it allowed for easy identification of single cells while maintaining a large field of view to minimize image acquisition time. Each 70×70 microwell array required 49 images per channel at this magnification with a 5% overlap of images. Image acquisition of a single array using bright field (100 ms camera exposure) plus 3 fluorescence channels (200 ms camera exposure each) required 216±4 s to complete (n=10). An autofocus algorithm was used to maintain focus for each image and required 99±2 s to complete. All of the automatically acquired focal planes were accurate to within the microscope objective's depth of field at 4× magnification (±21.8 µm) compared to the manually selected focal planes (n=50). The resulting total microwell array scan time (autofocus and image acquisition) was 315±5 s.

The locations of individual cell rafts were determined using the image processing and analysis software. Cell rafts containing a single $CD8^+$ cell were identified using CellTracker Deep Red fluorescence. These cell rafts were sorted based on the increase in Sytox Green fluorescence intensity. Automatically identified cell rafts were re-screened after gelatin encapsulation to ensure that a single CellTracker Deep Red-positive cell remained on the cell raft.

The automated system and processes enabled the measurement of the rates of T cell mediated killing for single cells, measured by fluorescence microscopy, was quantified in each cell raft with each cell raft designed to contain a population of fluorescently labeled antigen-presenting target cells and 1 $CD8^+$ T cell. This allowed for the identification of highly cytotoxic $CD8^+$ T cells in as little as 2 h. Cytotoxicity or cell killing was measured by summing the Sytox Green pixel intensity within the Hoechst fluorescence area on each cell raft. Using the Hoechst positive regions on each cell raft as a mask for the Sytox Green fluorescence greatly reduced spurious measurements due to debris and disintegrating cells and their fragments. The effector cell count and cytotoxicity information was recorded for each cell raft at each time point to generate temporal traces of cytotoxicity corresponding to specific numbers of effector cells present. The rates of target cell death among the individual $CD8^+$ T cells varied greatly; however, individual T cells maintained their rates of cytotoxicity throughout the time course of the experiment enabling rapid identification of highly cytotoxic $CD8^+$ T cells.

Upon completion of the cytotoxicity assay, the arrays were overlaid with a thin layer of gelatin as described previously. The incubator surrounding the microscope was cooled to 24° C. just prior to gelatin overlay of the array. The culture media above the array was replaced with 5 wt % bovine gelatin in PBS and the array was centrifuged. The array was then incubated for 10 min at 37° C., excess gelatin was aspirated and then incubated at 4° C. for 5 min to solidify the gelatin within the cell rafts. Cold (4° C.) culture media was overlaid onto the arrays. The cell raft with gel-encapsulated cell(s) is then readily captured by an overlaying magnetic wand dipped into the media above the array. The wand with the captured cell raft is then placed into the well of a 96-well plate facilitated by a magnet under the plate to pull the cell raft down to the bottom of the well.

Cell rafts that contained a $CD8^+$ T cell and showed a high rate of target cell death were individually released from the array using the needle-release device. Released rafts were then captured by a magnetic wand mounted on a computer controlled 3-axis motor and deposited into a 96-microwell plate in a similar manner to that described above with reference to FIG. 1. Cell rafts with highly active $CD8^+$ T cells were individually transferred to wells of a 96-well plate containing feeder cells, using a needle-release device coupled to the microscope. Three sorted T cells were clonally expanded. All three clones expressed high-avidity T cell receptors for M1p/HLA*02:01 tetramers.

This method can be used to determine the sequence of the T cell receptors (TCRs) in clones known to be cytotoxic to selected target cells and the data could be used for the development of immunotherapeutics. TCRs exist as heterodimeric protein complexes consisting of a TCRα chain paired with a TCRβ chain, which are expressed on the T cell's surface. The paired chains bind with high affinity to the target peptide/MHC, which were in this instance the M1p/HLA-A*02:01 complex. The portions of the TCRα and TCRβ chains that impart the specificity of the interaction with the target peptide/MHC are known as the CDR3 regions. If the CDR3 regions and flanking V and J segments of the TCRα and TCRβ chains are known, full-length transgenic TCR constructs can be produced and transfected into primary human T cells to change their specificity towards the target peptide/MHC. This approach could have a broad application in cancer immunotherapy where a cancer patient's T cells could be transduced with a transgenic TCR, containing TCRα and TCRβ chain sequences, which targets a cancer-specific peptide/MHC complex. The ability to determine the activity of small numbers of effector T cells in very short time scales could also be used for immune monitoring as T cell therapies are developed for clinical use. Such assays could be used to screen T cells cultures for antigen specificity against multiple antigens to reduce the risk of off-target cytotoxicity that has been observed in early T cell therapy studies. In addition, modifications of the array geometry can be easily modified to identify rare cytotoxic T cells, which could enable the identification and subsequent cloning of rare tumor antigen-specific CD8$^+$ T cells. Assays of this kind can alternatively be used to interrogate the effects of multiple cellular populations interacting at the same time such as studies investigating target cell resistance to T cell mediated cytotoxicity or the screening of drug candidates that modulate the activity of T cells.

A processor together with the actuator, camera, motors, magnet, and other components, as well as executable code can form the various means for carrying out an embodiment of the invention. In some embodiments, a general-purpose processor such as a DSP, microcontroller or microprocessor is used and non-transitory firmware, software, or microcode can be stored in a tangible storage device that is associated with the system. A self-contained computer such as a personal computer, mobile computer, or an embedded controller based system can be connected to the other hardware. Any such functionalities may be referred to herein as a "processor" or a "microprocessor." A storage device may be a memory integrated into the processor, or may be a memory chip that is addressed by the controller or processor to perform control functions. Such firmware, software or microcode is executable by the processor and when executed, causes the processor to perform its control functions. Such firmware or software could also be stored in or on a device such as an optical disk or traditional removable or fixed magnetic medium such as a disk drive connected to or within the cell isolation system.

It should be noted that any software as well as any data and information necessary to support the execution of instructions for any embodiment of the invention can be placed in a removable storage medium for development purposes or for maintenance and update purposes. Such a storage device may be accessed either directly or over a network, including the Internet.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

The invention claimed is:

1. An automated system comprising:
a computer system comprising at least one processor and memory;
an imaging device, comprising at least one imaging sensor, configured to obtain images of a microwell array, the microwell array comprising a plurality of cell rafts; and
an actuator configured to be controlled by the at least one processor, the actuator comprising a linear actuator or an autofocus motor of the imaging device, the linear actuator or the autofocus motor being configured to release cell rafts from the microwell array by actuating a release probe configured for individually releasing cell rafts from the microwell array;
wherein the automated system is configured for automated imaging and cell release, including the at least one processor being configured to:
obtain one or more images of the microwell array using the imaging device;
analyze the one or more images of the microwell array to identify a selected cell raft from among the plurality of cell rafts, wherein identifying the selected cell raft includes the at least one processor being further configured to count, for each cell raft, a number of cells depicted in a sub-image of the cell raft and identify at least one cell raft bearing a single isolated cell; and
control the actuator to release the selected cell raft from the microwell array.

2. The automated system of claim 1, comprising one or more motors configured to move the imaging device or the microwell array or both, wherein the computer system is configured to obtain the one or more images of the microwell array by performing an array scan, including the computer system configured to:
divide the microwell array into a plurality of fields of view such that the fields of view, collectively, include each of the cell rafts; and
for each field of view, control the one or more motors to orient the imaging device with the field of view of the microwell array and control the imaging device to obtain a respective image at the field of view.

3. The automated system of claim 2, comprising a microscope objective for the imaging device, and wherein, to obtain the one or more images of the microwell array, the computer system is further configured to, for each field of view, autofocus the microscope objective using one or more focus positions from at least one neighboring field of view.

4. The automated system of claim 3, wherein to autofocus the microscope objective, the computer system is further configured to sample a plurality of sample images at a plurality of sample focus positions and interpolate a current focus position from focus scores of the sample images.

5. The automated system of claim 1, wherein to determine the number of cells depicted in the sub-image, the computer system is further configured to:

apply an intensity threshold to the sub-image to create a binary image;
identify unique objects in the binary image; and
count the number of identified unique objects.

6. The automated system of claim 1, wherein to identify the single-cell raft, the computer system is configured to determine a confidence score indicating a degree of confidence in the determination that the single-cell raft houses the single isolated cell.

7. The automated system of claim 1, wherein to identify the selected cell raft, the computer system is configured to assign the selected cell raft to a mapped location of a collection plate.

8. The automated system of claim 7, further comprising a mechanical cell raft collector, wherein the at least one processor of the computer system is configured to send a first control signal to the mechanical cell raft collector to collect the selected cell raft after release from the microwell array and configured to send a second control signal to the mechanical cell raft collector to deposit the selected cell raft at the mapped location of the collection plate.

9. The automated system of claim 1, wherein the computer system is configured to determine an orientation or type of the microwell array based on the one or more images; and
wherein the computer system is to control the actuator to release the selected cell raft from the microwell array based on the orientation or type of the microwell array.

10. The automated system of claim 9, wherein the computer system is configured to determine the orientation or type of the microwell array based on an indicia coded into a specified corner of the microwell array.

11. The automated system of claim 1, wherein the automated system includes a gantry assembly comprising a second linear actuator configured to move a magnetic wand to collect the selected cell raft after release.

12. The automated system of claim 11, wherein the gantry assembly comprises a brightfield light emitting diode (LED) for illuminating the microwell array while the imaging device obtains images thereof.

13. The automated system of claim 1, further comprising:
a second linear actuator configured to move a magnetic wand to collect the selected cell raft; and
an automated stage to hold a collection plate to receive the selected cell raft from the magnetic wand, wherein the automated stage is a motorized stage configured to move the collection plate for receipt of the selected cell raft;
wherein the collection plate includes a collection magnet positioned underneath, the collection magnet having a polarization opposite that of the magnetic wand to repel a magnet in the magnetic wand and pull the selected cell raft to a bottom of the collection plate.

14. The automated system of claim 1, further comprising a microscope objective for the imaging system, wherein the release probe is aligned with an optical path of the microscope objective.

15. The automated system of claim 1, further comprising a microscope objective for the imaging system, wherein the release probe is offset from an optical path of the microscope objective such that the release probe does not intersect a field of view of the microscope objective.

16. The automated system of claim 15, wherein the offset is calibrated to be between a center of the field of view of the microscope objective and a puncture location of the release probe on the microwell array.

17. The automated system of claim 1, further comprising:
an automated stage to hold a collection plate to receive the selected cell raft from a magnetic wand of the automated system, wherein the automated stage is a motorized stage configured to move the collection plate for receipt of the selected cell raft;
wherein the collection plate includes a collection magnet positioned underneath, the collection magnet having a polarization opposite that of the magnetic wand to repel a magnet in the magnetic wand and pull the selected cell raft to a bottom of the collection plate.

* * * * *